(12) United States Patent
Kachlany

(10) Patent No.: US 10,149,889 B2
(45) Date of Patent: Dec. 11, 2018

(54) COMPOSITIONS FOR THE TREATMENT OF CANCER, AND METHODS FOR TESTING AND USING THE SAME

(71) Applicant: Rutgers, The State University of New Jersey, New Brunswick, NJ (US)

(72) Inventor: Scott Kachlany, Bridgewater, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 15/082,626

(22) Filed: Mar. 28, 2016

(65) Prior Publication Data
US 2016/0243191 A1 Aug. 25, 2016
US 2018/0071360 A9 Mar. 15, 2018

Related U.S. Application Data

(60) Continuation-in-part of application No. 14/563,421, filed on Dec. 15, 2014, now Pat. No. 9,295,710, which is a division of application No. 13/446,949, filed on Apr. 13, 2012, now Pat. No. 8,926,990, which is a continuation-in-part of application No. PCT/US2010/056864, filed on Nov. 16, 2010, and a continuation-in-part of application No. PCT/US2010/052453, filed on Oct. 3, 2010, application No. 15/082,626, which is a continuation-in-part of application No. 14/024,110, filed on Sep. 11, 2013, now abandoned, which is a continuation of application No. 13/446,949, and a continuation of application No. 13/241,683, filed on Sep. 23, 2011, now abandoned, which is a continuation of application No. 12/154,843, filed on May 27, 2008, now Pat. No. 8,053,406, which is a continuation-in-part of application No. 12/150,038, filed on Apr. 23, 2008, now abandoned, and a continuation-in-part of application No. PCT/US2006/045258, filed on Nov. 25, 2006, application No. 15/082,626, which is a continuation-in-part of application No. 14/005,372, filed as application No. PCT/US2012/029476 on Mar. 16, 2012, now Pat. No. 9,352,017.

(60) Provisional application No. 61/261,984, filed on Nov. 17, 2009, provisional application No. 61/285,378, filed on Dec. 10, 2009, provisional application No. 61/251,171, filed on Oct. 13, 2009, provisional application No. 60/925,794, filed on Apr. 23, 2007, provisional application No. 60/739,537, filed on Nov. (Continued)

(51) Int. Cl.
*A61K 38/16* (2006.01)
*A61K 45/06* (2006.01)
*A61K 39/395* (2006.01)
*A61K 31/136* (2006.01)
*A61K 31/196* (2006.01)
*A61K 31/198* (2006.01)
*G01N 33/574* (2006.01)
*G01N 33/50* (2006.01)
*G01N 33/569* (2006.01)
*A61K 31/704* (2006.01)
*A61K 31/7068* (2006.01)
*A61K 31/7076* (2006.01)

(52) U.S. Cl.
CPC .......... *A61K 38/164* (2013.01); *A61K 31/136* (2013.01); *A61K 31/196* (2013.01); *A61K 31/198* (2013.01); *A61K 31/704* (2013.01); *A61K 31/7068* (2013.01); *A61K 31/7076* (2013.01); *A61K 39/3955* (2013.01); *A61K 45/06* (2013.01); *G01N 33/5052* (2013.01); *G01N 33/56972* (2013.01); *G01N 33/574* (2013.01); *G01N 2800/52* (2013.01); *G01N 2800/709* (2013.01); *G01N 2800/7095* (2013.01); *Y10S 530/825* (2013.01)

(58) Field of Classification Search
CPC .............. A61K 2300/00; A61K 38/164; A61K 31/136; A61K 31/704; A61K 31/196; A61K 31/198; A61K 31/7068; A61K 31/7076; A61K 45/06; A61K 31/255; A61K 31/506; A61K 31/7048; A61K 39/3955; C07K 14/195; G01N 2800/52; G01N 2800/709; G01N 2800/7095; G01N 33/5052; G01N 33/56972; G01N 33/574; Y10S 530/825
See application file for complete search history.

(56) References Cited

U.S. PATENT DOCUMENTS 9,352,017 B2 * 5/2016 Kachlany ............. C07K 14/195
2005/0032217 A1 2/2005 Zadeh
(Continued)

FOREIGN PATENT DOCUMENTS

WO 97/16531 A1 5/1997
WO 2014210454 A1 12/2014

OTHER PUBLICATIONS

DiFranco et al. Leuk. Res. 39: 649-656, Epub Mar. 21, 2015.*
(Continued)

*Primary Examiner* — Sarvamangala Devi
(74) *Attorney, Agent, or Firm* — Fox Rothschild LLP

(57) ABSTRACT

The invention relates to pharmaceutical compositions comprising leukotoxin, including methods to treat lymphoma, and methods to diagnose lymphoma. The lymphoma includes lymphoma cells expressing activated LFA-1, and the leukotoxin binds to the activated LFA-1 on the lymphoma cells and destroys the lymphoma cells by apoptosis or necrosis, thereby treating said lymphoma.

4 Claims, 9 Drawing Sheets

Specification includes a Sequence Listing.

Related U.S. Application Data 25, 2005, provisional application No. 61/453,162, filed on Mar. 16, 2011.

(56) References Cited

U.S. PATENT DOCUMENTS

| | | | |
|---|---|---|---|
| 2007/0043012 A1* | 2/2007 | Bridger | A61K 31/255 514/183 |
| 2009/0075883 A1 | 3/2009 | Kachlany | |
| 2011/0039863 A1 | 2/2011 | Hilberg et al. | |
| 2011/0053893 A1 | 3/2011 | Wu et al. | |

OTHER PUBLICATIONS

Diaz et al, Microbial Pathogenesis, published Jan. 2006, 40:48-55.
Kaplan et al, J Clin Microbiol, 2002, 40:1181-1187.
Pasechnik, Exp Opin Invest, Drugs, 2000, 9:1243-1256.
Tomkinson et al, Leuk Res, 2003, 27:1039-1050.
Tsai et al., Extraction and Isolation of a Leukotoxin from Actinobacillus actinomycetemcomitans with Polymyxin B, Infection and Immunity, 43:700-705 (1984).
Simpson et al., Killing of Human Myelomonocytic Leukemia and Lymphocytic Cell Lines by Actinobacillus actinomycetemcomitans Leukotoxin, Infection and Immunity, 56:1162-1166 (1988).
Fukunaga et al., Actinobacillus actinomycetemcomitans induces lethal effects on the macrophage-like human cell line U937, 16:284-289 (2001).
Balashova et al., "Leukotoxin confers beta-hemolytic activity to Actinobacillus actinomycetemcomitans", Infection and Immunity, 74(4):2015-2021, 2006.
DiRienzo et al., "Monoclonal antibodies to leukotoxin of Actinobacillus actinomycetemcomitans", Infection and Immunity, 47(1):31-36, 1985.
Hormozi et al., "Target cell specificity of the Pasteurella haemolytica leukotoxin is unaffected by the nature of the fatty-acyl group used to activate the toxin in vitro", FEMS Microbiology Letters, 169:139-145, 1998.
Lally et al., "RTX toxins recognize a .beta.2 integrin on the surface of human target cells", The Journal of Biological Chemistry, 272(48):30463-30469, 1997.
Linhartova et al., "RTX proteins: a highly diverse family secreted by a common mechanism", FEMS Microbiol Rev, 1-37, 2010 (E pub ahead of print).
Ohta et al., "Nuclease-sensitive binding of an Actinobacillus actinomycetemcomitans leukotoxin to the bacterial cell surface", Infection and Immunity, 59(12):4599-4605, 1991.
Taichman et al., Biochemical and morphological characterization of the killing of human monocytes by a leukotoxin derived from Actinobacillus actinomycetemcomitans, Infection and Immunity, 28(1):258-268, 1980.
Thumbikat et al., "Biological effects of two genetically defined leukotoxin mutants of Mannheimia haemolytica", Microbial Pathogenesis 34:217-226; 2003.
Spitznagel et al., "Regulation of leukotoxin in leukotoxic and nonleukotoxic strains of Actinobacillus actinomycetemcomitans", Infection and Immunity, 59(4):1394-1401, 1991.
Kachlany, S. C. et al., 2010. "Anti-leukemia activity of a bacterial toxin with natural specificity for LFA-1 on white blood cells", Leukemia Research 34:777-85.
DesJardin et al. "*Mycobacterium tuberculosis*-infected human macrophages exhibit enhanced cellular adhesion with Increased expression of LFA-1 and ICAM-1 and reduced expression and/or function of complement receptors, FcgammaRII and the mannose receptor", Microbiology 2002; 148: 3161-3171.
Guttman-Yassky et al. 2008. "Blockade of CD11 a by efalizumab in psoriasis patients induces a unique state of T-cell hyporesponsiveness", The Journal of Investigative Dermatology, 128(5): 1182-1191.
P- Giblin et al. 2006. "LFA-1 as a Key Regulator of Immune Function: Approaches toward the Development of LFA-1-Based Therapeutics", Current Pharmaceutical Design 12(22): 2771-2795.
Shamik Ghosh et al. 2006. "The LFA-1 adhesion molecule is required for protective immunity during pulmonary *Mycobacterium tuberculosis* infection", The Journal of Immunology 176(8): 4914-4922.
Dileepan et al. Infect. Immun. 75:4851-4856, Jul. 16, 2007.
Walker, et al.: "Toward an AIDS Vaccine", Science, May 9, 2008, vol. 320, pp. 760-764.
Pantaleo, et al: "Correlates of Immune Protection in HIV-1 Infection: What We Know, What We Don't Know, What We Should Know", Nature Medicine, Aug. 2004, vol. 10, No. 8, pp. 806,810.
"Understanding HIV Drug Resistance", Global Campaign for Microbicides, 2009, pp. 1-2.
Tuen et al.: Abstracts from AIDS Vaccine 2010, Abstract P15.02 A Bacterial Leukotoxin for the Prevention of HIV Infection by Selective Killing of CD4 T Cells Targeted by HIV, AIDS Research and Human Retroviruses, 2010, vol. 26, No. 10, p. A-91.
Swiss-Prot Accession# Q43892. Created Oct. 31, 2006 (online). [Retrieved on Jan. 27, 2011 (Jan. 27, 2011)]. Retrieved from the Internet <URL: http://www.ncbi.nlm.nih.gov/protein/Q43892>.
Elovaara, et al: "Adhesion Molecules in Multiple Sclerosis" Arch. Neurol., Apr. 2000, vol. 57, pp. 546-551.
Kachlany, S.C, et al., "Secretion of RTX Leukotoxin by Actinobacillus Actinomycetemcomitans," Infect Immun, Nov. 2000, vol. 68, issue 11, pp. 6094-6100.
Kachlany, S.C., et al., "Purification of Secreted Laukotoxin (LtxA) from Actinobacillus antinomysetemcomitans," Protein Expr Purif, 2002, vol. 25, No. 3, pp. 465-471 (Abstract).
Kachlany, S. C., "Aggregatibacter Actinomycetemcomitans Leukotoxin: From Threat to Therapy," J. Dent Res, 2010, vol. 89, No. 6, pp. 561-570.
Kachlany, S. C. et al., "Anti-Leukemia Activity of a Bacterial Toxin With Natural Specificity for LFA-1 on White Blood Cells," Leuk Res, 2010, vol. 34, No. 6, pp. 777-785.
Mangan, D. F., et al., "Lethal Effects of Actinobacillus Actinomycetemcomitans Leukotoxin on Human T Lymphocytes," Infect Immun., Sep. 1991, vol. 59, No. 9, pp. 3267-3272.
Schechter, T., et al., "Pharmacokinetic disposition and clinical outcomes in infants and children receiving intravenous busulfan for allogeneic hematopoietic stem cell transplantation," Biol., Blood Marrow Transplant, Mar. 2007, vol. 13, No. 3, pp. 307-314 (Abstract).
Wang, Y., et al., "Effects of Imatinib (Glivec) on the Pharmacolinetics of Metoprolol, a CYP2D6 Substrate, in Chinese Patients with Chronic Myelogenous Laukaemia," B J Clin Pharmacol, 2008, vol. 65, No. 6, pp. 885-892.
Kreitman et al: Synergistic Targeting of Leukemia with Leukotoxin and Chemotherapy; Leukemmia Research, 2001, vol. 35, pp. 1438-1439.
Gupta et al: "In Vitro Synergism Between LFA-1 Targeting Leukotoxin (Leukothera TM) and Standard Chemotherapeutic Agents in Leukemia Cells", Leukemia Research, 2001, vol. 35, pp. 1498-1505.
EL-Gabalawy et al: "Synovial Distribution of Alpha-d/CD18, A Novel Leukointegrin", Arthritis & Rheumatism, Nov. 1996, vol. 39, No. 11, pp. 1913-1921.

* cited by examiner

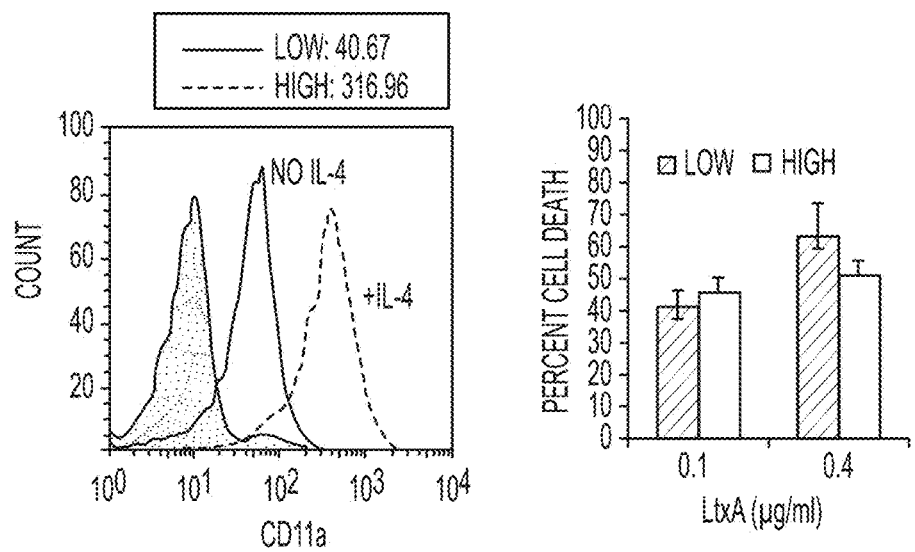
FIG. 5A
FIG. 5B
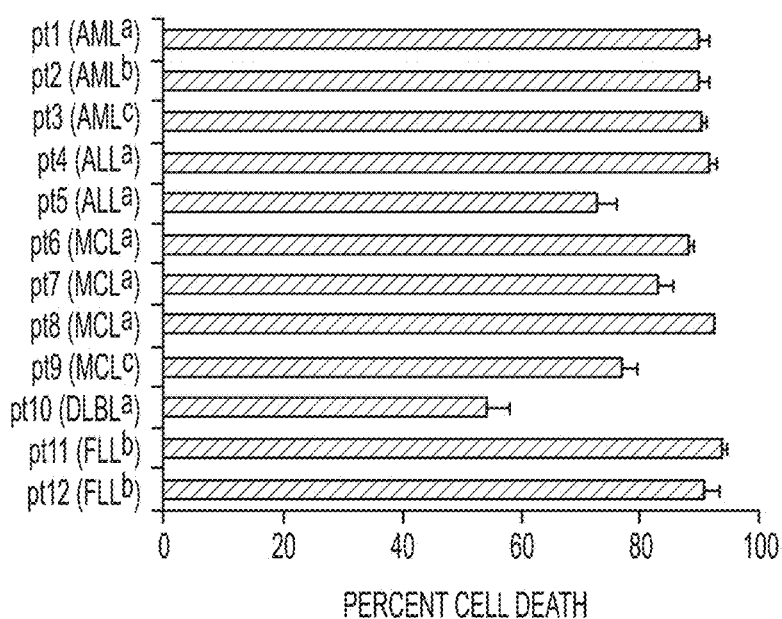
FIG. 6

SEQUENCE LISTING

```
<160> NUMBER OF SEQ ID NOS: 2

<210> SEQ ID NO 1
<211> LENGTH: 1055
<212> TYPE: PRT
<213> ORGANISM: Aggregatibacter actinomycetemcomitans

<400> SEQUENCE: 1

Met Ala Thr Thr Ser Leu Leu Asn Thr Lys Gln Gln Ala Ala Gln Phe
1               5                   10                  15

Ala Asn Ser Val Ala Asp Arg Ala Lys Glu Asn Ile Asp Ala Ala Lys
            20                  25                  30

Glu Gln Leu Gln Lys Ala Leu Asp Lys Leu Gly Lys Thr Gly Lys Lys
```

```
                    35                  40                  45
Leu Thr Leu Tyr Ile Lys Asn Tyr Lys Lys Gly Asn Gly Leu Thr Ala
 50                  55                  60

Leu Ile Lys Ala Ala Gln Lys Leu Gly Ile Glu Val Tyr His Glu Gly
 65                  70                  75                  80

Lys Asp Gly Pro Ala Leu Thr Asn Gly Ile Leu Asn Thr Gly Lys Lys
                 85                  90                  95

Leu Leu Gly Leu Thr Glu Arg Gly Leu Thr Leu Phe Ala Pro Glu Leu
                100                 105                 110

Asp Lys Trp Ile Gln Gly Asn Lys His Leu Ser Asn Ser Val Gly Ser
            115                 120                 125

Thr Gly Asn Leu Thr Lys Ala Ile Asp Lys Val Gln Ser Val Leu Gly
            130                 135                 140

Thr Leu Gln Ala Phe Leu Asn Thr Ala Phe Ser Gly Met Asp Leu Asp
145                 150                 155                 160

Ala Leu Ile Lys Ala Arg Gln Asn Gly Lys Asn Val Thr Asp Val Gln
                165                 170                 175

Leu Ala Lys Ala Ser Leu Asn Leu Ile Asn Glu Leu Ile Gly Thr Ile
            180                 185                 190

Ser Ser Ile Thr Asn Asn Val Asp Thr Phe Ser Lys Gln Leu Asn Lys
        195                 200                 205

Leu Gly Glu Ala Leu Gly Gln Val Lys His Phe Gly Ser Phe Gly Asp
210                 215                 220

Lys Leu Lys Asn Leu Pro Lys Leu Gly Asn Leu Gly Lys Gly Leu Gly
225                 230                 235                 240

Ala Leu Ser Gly Val Leu Ser Ala Ile Ser Ala Ala Leu Leu Leu Ala
                245                 250                 255

Asn Lys Asp Ala Asp Thr Ala Thr Lys Ala Ala Ala Ala Glu Leu
            260                 265                 270

Thr Asn Lys Val Leu Gly Asn Ile Gly Lys Ala Ile Thr Gln Tyr Leu
            275                 280                 285

Ile Ala Gln Arg Ala Ala Ala Gly Leu Ser Thr Thr Gly Pro Val Ala
290                 295                 300

Gly Leu Ile Ala Ser Val Val Ser Leu Ala Ile Ser Pro Leu Ser Phe
305                 310                 315                 320

Leu Gly Ile Ala Lys Gln Phe Asp Arg Ala Arg Met Leu Glu Glu Tyr
                325                 330                 335

Ser Lys Arg Phe Lys Lys Phe Gly Tyr Asn Gly Asp Ser Leu Leu Gly
            340                 345                 350

Gln Phe Tyr Lys Asn Thr Gly Ile Ala Asp Ala Ala Ile Thr Thr Ile
            355                 360                 365

Asn Thr Val Leu Ser Ala Ile Ala Ala Gly Val Gly Ala Ala Ser Ala
            370                 375                 380

Gly Ser Leu Val Gly Ala Pro Ile Gly Leu Leu Val Ser Ala Ile Thr
385                 390                 395                 400

Ser Leu Ile Ser Gly Ile Leu Asp Ala Ser Lys Gln Ala Val Phe Glu
                405                 410                 415

His Ile Ala Asn Gln Leu Ala Asp Lys Ile Lys Ala Trp Glu Asn Lys
            420                 425                 430

Tyr Gly Lys Asn Tyr Phe Glu Asn Gly Tyr Asp Ala Arg His Ser Ala
            435                 440                 445

Phe Leu Glu Asp Ser Leu Lys Leu Phe Asn Glu Leu Arg Glu Lys Tyr
            450                 455                 460
```

```
Lys Thr Glu Asn Ile Leu Ser Ile Thr Gln Gln Gly Trp Asp Gln Arg
465                 470                 475                 480

Ile Gly Glu Leu Ala Gly Ile Thr Arg Asn Gly Asp Arg Ile Gln Ser
                485                 490                 495

Gly Lys Ala Tyr Val Asp Tyr Leu Lys Lys Gly Glu Glu Leu Ala Lys
            500                 505                 510

His Ser Asp Lys Phe Thr Lys Gln Ile Leu Asp Pro Ile Lys Gly Asn
        515                 520                 525

Ile Asp Leu Ser Gly Ile Lys Gly Ser Thr Thr Leu Thr Phe Leu Asn
    530                 535                 540

Pro Leu Leu Thr Ala Gly Lys Glu Glu Arg Lys Thr Arg Gln Ser Gly
545                 550                 555                 560

Lys Tyr Glu Phe Ile Thr Glu Leu Lys Val Lys Gly Arg Thr Asp Trp
                565                 570                 575

Lys Val Lys Gly Val Pro Asn Ser Asn Gly Val Tyr Asp Phe Ser Asn
            580                 585                 590

Leu Ile Gln His Ala Val Thr Arg Asp Asn Lys Val Leu Glu Ala Arg
        595                 600                 605

Leu Ile Ala Asn Leu Gly Ala Lys Asp Asp Tyr Val Phe Val Gly Ser
    610                 615                 620

Gly Ser Thr Ile Val Asn Ala Gly Asp Gly Tyr Asp Val Val Asp Tyr
625                 630                 635                 640

Ser Lys Gly Arg Thr Gly Ala Leu Thr Ile Asp Gly Arg Asn Ala Thr
                645                 650                 655

Lys Ala Gly Gln Tyr Lys Val Glu Arg Asp Leu Ser Gly Thr Gln Val
            660                 665                 670

Leu Gln Glu Thr Val Ser Lys Gln Glu Thr Lys Arg Gly Lys Val Thr
        675                 680                 685

Asp Leu Leu Glu Tyr Arg Asn Tyr Lys Leu Asp Tyr Tyr Tyr Thr Asn
    690                 695                 700

Lys Gly Phe Lys Ala His Asp Glu Leu Asn Ser Val Glu Glu Ile Ile
705                 710                 715                 720

Gly Ser Thr Leu Arg Asp Lys Phe Tyr Gly Ser Lys Phe Asn Asp Val
                725                 730                 735

Phe His Gly His Asp Gly Asp Leu Ile Tyr Gly Tyr Asp Gly Asp Asp
            740                 745                 750

Asp Arg Leu Tyr Gly Asp Asn Gly Asn Asp Glu Ile His Gly Gly Gln
        755                 760                 765

Gly Asn Asp Lys Leu Tyr Gly Gly Ala Gly Asn Asp Arg Leu Phe Gly
    770                 775                 780

Glu Tyr Gly Asn Asn Tyr Leu Asp Gly Gly Glu Gly Asp Asp His Leu
785                 790                 795                 800

Glu Gly Gly Asn Gly Ser Asp Ile Leu Arg Gly Gly Ser Gly Asn Asp
                805                 810                 815

Lys Leu Phe Gly Asn Gln Gly Asp Leu Leu Asp Gly Gly Glu Gly Gly
            820                 825                 830

Asp Asp Gln Leu Ala Gly Gly Glu Gly Asn Asp Ile Tyr Val Tyr Arg
        835                 840                 845

Lys Glu Tyr Gly His His Thr Ile Thr Glu His Ser Gly Asp Lys Asp
    850                 855                 860

Lys Leu Ser Leu Ala Asn Ile Asn Leu Lys Asp Val Ser Phe Glu Arg
865                 870                 875                 880
```

```
          Asn Gly Asn Asp Leu Leu Lys Thr Asn Asn Arg Thr Ala Val Thr
                          885                 890                 895
          Phe Lys Gly Trp Phe Ser Lys Pro Asn Ser Ser Ala Gly Leu Asp Glu
          900                 905                 910
          Tyr Gln Arg Lys Leu Leu Glu Tyr Ala Pro Glu Lys Asp Arg Ala Arg
                      915                 920                 925
          Leu Lys Arg Gln Phe Glu Leu Gln Arg Gly Lys Val Asp Lys Ser Leu
              930                 935                 940
          Asn Asn Lys Val Glu Glu Ile Ile Gly Lys Asp Gly Glu Arg Ile Thr
          945                 950                 955                 960
          Ser Gln Asp Ile Asp Asn Leu Phe Asp Lys Ser Gly Asn Lys Lys Thr
                          965                 970                 975
          Ile Ser Pro Gln Glu Leu Ala Gly Leu Ile Lys Asn Lys Gly Lys Ser
                      980                 985                 990
          Ser Ser Leu Met Ser Ser Ser Arg Ser Ser Ser Met Leu Thr Gln Lys
              995                 1000                1005
          Ser Gly Leu Ser Asn Asp Ile Ser Arg Ile Ile Ser Ala Thr Ser
              1010                1015                1020
          Gly Phe Gly Ser Ser Gly Lys Ala Leu Ser Ala Ser Pro Leu Gln
              1025                1030                1035
          Thr Asn Asn Asn Phe Asn Ser Tyr Ala Asn Ser Leu Ala Thr Thr
              1040                1045                1050
          Ala Ala
              1055

<210> SEQ ID NO 2
<211> LENGTH: 3168
<212> TYPE: DNA
<213> ORGANISM: Aggregatibacter actinomycetemcomitans

<400> SEQUENCE: 2
atggcaacta cttcactgct aaatacaaaa cagcaagctg cacagtttgc aaattcagtt      60
gcagatagag ctaaggaaaa tattgatgct gcaaaagaac aattgcaaaa ggcgttagat     120
aaattaggga agacaggtaa gaaattaact ttatatatcc ctaagaatta caaaaaagga     180
aatggtctta ctgcgcttat aaaagcagca cagaagttag ggattgaagt atatcatgaa     240
gggaaagacg gcccggcatt aactaatggt attttaaata ctgggaaaaa attacttggt     300
cttaccgaac gaggtttaac tttatttgct ccggaattag ataaatggat tcaaggtaat     360
aaacatttaa gtaattctgt gggtagtact ggaaatttga caaaagcgat agataaggtt     420
cagagtgttc ttggtacgtt acaagcgttt ttgaacaccg cattttcggg catggattta     480
gatgccttaa ttaaagcccg tcaaaatggt aaaaatgtaa cagatgtaca gctagcaaaa     540
gccagtctta acctgattaa tgaattgatt ggtactattt ctagcattac aaataatgta     600 gatactttt ctaaacaact taataagtta ggtgaagcac taggacaagt aaaacatttt     660
ggtagttttg gagataaatt aaagaattta cctaagttag gtaatcttgg aaaaggttta     720
ggtgcattat ccggtgtatt gtcggctata tcagcggctc tattacttgc aaataaagat     780
gctgatactg caacgaaagc agcggctgca gctgaattga caaataaagt gctaggtaac     840
atcggtaaag cgatcacaca atacttgatt gctcaacgtg ctgcagcggg gctttctact     900
acgggacctg tcgcagggtt aattgcctct gtggtcagct ggcaatcag ccctttgtct     960 ttcctaggta ttgcgaaaca atttgatcgt gcgagaatgc ttgaggaata ctcgaaacgc    1020
tttaagaaat ttggttataa cggcgatagt ttacttggtc aattctacaa aaatacaggg    1080
```

```
atcgcagatg ctgcgattac aacgattaac actgtattaa gtgctattgc agcagggggtt    1140 ggtgcagcct ccgccggttc tttagttggt gcgccaatcg gtttgttagt gagtgcgatt    1200
accagcttaa tttcaggaat tcttgatgct tctaaacaag ccgttttttga acatatcgcg   1260 aatcagctcg ccgataaaat taaagcatgg gagaataagt acggtaagaa ttactttgaa    1320
aatggctatg atgcccgtca ttccgccttc ttggaagatt cactaaaatt atttaatgag    1380
ttacgtgaaa aatataaaac cgaaaatata ttatctatca ctcaacaagg ttgggatcag    1440
cgcattggtg aattagcagg tatcactcgt aatggagatc gtattcaaag tggtaaagct    1500
tatgtggatt atttgaaaaa gggtgaggag cttgcaaagc atagcgataa attcactaaa    1560
cagattttag atccaatcaa aggtaatatt gatctttcgg gtataaaagg ttctaccact    1620 ctaactttt taaatccgtt gttaaccgca ggtaaggaag aacggaaaac acgtcagtca    1680
ggtaaatatg aatttattac tgaattaaaa gtaaaaggac gtaccgattg gaaggtaaaa    1740
ggtgttccta attctaatgg tgtatatgat ttttctaact taattcaaca tgccgttaca    1800
cgtgataata aagttctaga agcaagatta attgctaatt tgggtgctaa agatgattat    1860 gttttttgtcg gatccggttc aacaatagtt aatgctggag acggttatga tgtggtggac    1920
tatagtaaag gtcgcaccgg tgcattaaca atcgacggtc gtaatgctac taaagccgga    1980
caatataagg ttgaaagaga tcttagcggt actcaagtct tgcaggaaac cgtatcaaag    2040
caagaaacta aacgagggaa ggttaccgat ctacttgaat atcgtaacta taaattagat    2100
tactattata cgaataaggg ctttaaagct catgatgaat taaactcagt agaggaaatt    2160
atcggcagca cactacgtga taaattttat ggttctaaat ttaatgatgt tttccatggt    2220
cacgatggcg atgatttgat ttatggttat gatggcgatg atcgtttgta tggcgataat    2280
gggaatgacg aaattcatgg cggccaaggt aatgataagc tctatggtgg tgccggtaac    2340
gataggctct ttggtgaata tggcaacaac tatcttgacg gtggagaagg cgacgaccac    2400
ttagagggag gcaatggttc cgatattcta agaggtggaa gtggcaatga taagttgttt    2460
ggaaaccaag gagatgattt acttgacggt ggagaaggcg atgaccaact tgccggtgga    2520
gaaggaaatg atatttatgt ttaccgtaaa gaatatgggc accacactat tacgaacat    2580 agcggtgata aagataaatt atcattagca aatatcaatc tcaaagatgt gtcatttgag    2640
cgtaacggca atgatctact attgaaaaca ataatagaa cagcagtaac atttaaagga    2700
tggtttagta aacctaattc atcggcagga ttagatgagt atcaaagaaa acttcttgaa    2760
tacgcacctg aaaaggatcg tgcacgactt aagagacaat ttgagttaca gcgaggtaaa    2820
gtcgacaaat cactcaataa taaagttgaa gaaattatcg gtaaagatgg ggagcggatt    2880
acttcgcaag acattgataa tcttttttgat aagagtggga acaaaaagac aatttcacct    2940
caagagcttg ccggacttat taagaataaa ggtaagtcaa gtagccttat gtcttcttct    3000
cgttcgtcaa gtatgcttac acaaaagtcc ggtttgtcaa atgatattag tcgtattatt    3060
tcagcaacca gtggtttttgg ttcatccggt aaagcgttat ccgcttcgcc attgcagacc    3120
aataataact ttaactctta cgcaaattcg ttagcaacta ctgcggcc                 3168
```

COMPOSITIONS FOR THE TREATMENT OF CANCER, AND METHODS FOR TESTING AND USING THE SAME

CROSS REFERENCE TO RELATED APPLICATIONS

The present application is a Continuation In Part of U.S. patent application Ser. No. 14/024,110, filed Sep. 11, 2013, now abandoned, which is a Continuation of U.S. patent application Ser. No. 13/241,683, filed Sep. 23, 2011, now abandoned, which is a Continuation of U.S. patent application Ser. No. 12/154,843, filed May 27, 2008, now U.S. Pat. No. 8,053,406, which is a Continuation In Part of PCT Application No. PCT/US2006/045258, filed Nov. 25, 2006, which, in turn, claims priority under 35 U.S.C. § 119(e) from U.S. Provisional Application Ser. No. 60/739,537, filed Nov. 25, 2005; and U.S. Non-Provisional application Ser. No. 12/150,038, filed Apr. 23, 2008, now abandoned, which, in turn, claims priority under 35 U.S.C. § 119(e) from U.S. Provisional Application Ser. No. 60/925,794, filed Apr. 25, 2007. U.S. patent application Ser. No. 14/024,110 is also a Continuation In Part of U.S. patent application Ser. No. 13/446,949, filed on Apr. 13, 2012, now granted as U.S. Pat. No. 8,926,990, which is a Continuation In Part of PCT Application No. PCT/US2010/052453, filed Oct. 13, 2010, which claims priority under 35 U.S.C. § 119(e) from U.S. Provisional Application Ser. No. 61/251,171, filed Oct. 13, 2009 and 61/285,378, filed Dec. 10, 2009. U.S. patent application Ser. No. 13/446,949 is also a Continuation In Part of PCT Application No. PCT/US2010/056864, filed Nov. 16, 2010, which claims priority under 35 U.S.C. § 119(e) from U.S. Provisional Application Ser. No. 61/261,984, filed Nov. 17, 2009. The present application is also a Continuation In Part of U.S. patent application Ser. No. 14/563,421, filed Dec. 15, 2014, now granted as U.S. Pat. No. 9,295,710, which is a Divisional of U.S. patent application Ser. No. 13/446,949, filed on Apr. 13, 2012, now granted as U.S. Pat. No. 8,926,990. The present application is also a Continuation In Part of U.S. patent application Ser. No. 14/005,372, filed Nov. 13, 2013, now granted as U.S. Pat. No. 9,352,017, which is a National Stage Entry of PCT Application No. PCT/US2012/029476, filed Mar. 16, 2012, which, in turn, claims priority under 35 U.S.C. § 119(e) from U.S. Provisional Application Ser. No. 61/453,162, filed Mar. 16, 2011.

The present application is also a Continuation In Part of U.S. patent application Ser. No. 14/563,421, filed Dec. 15, 2014, now granted as U.S. Pat. No. 9,295,710, which is a division of U.S. patent application Ser. No. 13/446,949, filed on Apr. 13, 2012, now granted as U.S. Pat. No. 8,926,990, which is a Continuation In Part of PCT Application No. PCT/US2010/052453, filed Oct. 13, 2010, which claims priority under 35 U.S.C. § 119(e) from U.S. Provisional Application Ser. Nos. 61/251,171, filed Oct. 13, 2009 and 61/285,378, filed Dec. 10, 2009. U.S. patent application Ser. No. 13/446,949 is also a Continuation In Part of PCT Application No. PCT/US2010/056864, filed Nov. 16, 2010, which claims priority under 35 U.S.C. § 119(e) from U.S. Provisional Application Ser. No. 61/261,984, filed Nov. 17, 2009.

The entire contents of the aforementioned listed applications are incorporated by reference herein.

RELATED FEDERALLY SPONSORED RESEARCH

The work described in this application was sponsored at least in part, under Grant No. RO1 DE16133, from the National Institute of Dental and Craniofacial Research, and under Grant No. NIH RO1DE16133, from the National Institutes of Health. Accordingly, the Government has certain rights in the invention.

FIELD OF THE INVENTION

The invention relates to pharmaceutical compositions comprising leukotoxin, a chemotherapeutic agent, including methods to treat cancer, and methods to induce apoptosis. More particularly, the agents and compositions comprise a repeat in toxin (RTX) molecule that demonstrates leukocyte specificity, and that specifically targets cancer cells, such as lymphoma cells, either taken from a patient or derived from a cell line.

BACKGROUND OF THE INVENTION

Bacteria and their toxins have been investigated for their anticancer activities. In the 1970s, bacteria (such as non-pathogenic Clostridium) were used for the treatment of malignant brain tumors, but the tumors recurred in these brain tumor patients. More than 100 microorganisms have been studied for their potential anticancer activities, and many bacteria have growth specificity for tumors that is 1000 times greater than for other tissue.

Receptor-specific biological agents have an advantage over traditional chemotherapy cancer drugs in that they exhibit greater disease specificity and lower toxicity. While their anti-tumor activities make many bacteria attractive therapeutic agents, there are inherent risks to administering live bacteria to humans. A safer and more effective strategy has been to use biological toxins, specifically from bacteria, as therapeutic agents. Bacterial toxins are not only toxic, but are also highly specific for certain cell types, or can be engineered to be specific by fusing the toxin to other molecules. Many bacterial toxins are able to enter mammalian cells where they exert their toxic effects. Because of extensive evolutionary adaptation between bacteria and their hosts, bacteria have become very good at "developing" highly effective toxins.

Each year, more than 60,500 people die of hematologic malignancies (leukemia, lymphoma, myeloma) with more than 110,000 new annual diagnoses in the US alone. B-cell related cancers include Hodgkin's, and non-Hodgkin's lymphoma (NHL) (e.g., mantle cell lymphoma (MCL), follicular lymphoma (FL), diffuse large B-cell lymphoma (DLBCL), and Burkitt lymphoma). Current treatment for these cancers includes the use of synthetic compounds that target the cell division process of nearly all cells of the body, not just the cancerous ones. As a result, devastating side effects are all too common. Furthermore, a significant percentage of patients eventually show resistance to many of the drugs, thus rendering treatment largely ineffective or susceptible to the incidence of relapse and refractory disease for many patients remains high. For example, MCL is a deadly and incurable disease and even with new therapeutic approaches, the mean overall survival rate remains approximately 3-4 years. For FL, the most common indolent NHL, there is no consensus treatment protocol and the disease is considered incurable. Approximately 30-40% of DLBCL patients still die from this cancer. Most of these deaths result from therapeutic resistance in the cancerous cells when the disease recurs. Thus, there is a great need for novel agents that target B-cell lymphomas. While the drugs currently in use are toxic for cells, they are not highly specific. A new class of therapeutic agents for the treatment of hematologic malignancies, and cancer in general, includes drugs that exhibit specificity for predominantly the cancerous cell type. Examples of targeted therapeutics include Rituximab, which is a monoclonal antibody against B-lymphocytes, and Mylotarg, an antibody-anti-tumor antibiotic fusion directed against cells of myelomonocytic lineage.

*Actinobacillus actinomycetemcomitans* is a Gram negative pathogen that inhabits the oral cavities of humans. *A. actinomycetemcomitans* is the etiologic agent of localized aggressive periodontitis (LAP), a rapidly progressing and destructive disease of the gingiva and periodontal ligaments. Among its many virulence factors, *A. actinomycetemcomitans* produces an RTX (repeats in toxin) leukotoxin. *A. actinomycetemcomitans* leukotoxin is an approximately 115 kDa protein that kills specifically leukocytes of humans and Old World Primates. Leukotoxin (LtxA) is part of the RTX family that includes *E. coli* a-hemolysin (H1yA) and Bordetella pertussis adenylate cyclase (CyaA). Leukotoxin may play an important role in *A. actinomycetemcomitans* pathogenesis by helping the bacterium destroy gingival crevice polymorphonuclear leukocytes (PMNs) and monocytes, resulting in the suppression of local immune defenses.

LtxA binds leukocyte function antigen (LFA-1) on white blood cells (WBCs) and induces cell death via apoptosis or necrosis. It has been found that LtxA preferentially targets WBCs with high levels of activated LFA-1, a characteristic of many leukemias and lymphomas. In many ways, LtxA represents a natural version of an immunotoxin since it is both toxic and highly specific within the same molecule. Advantages of native LtxA over artificially-engineered molecules include greater stability, increased specificity, and lower toxicity.

The U.S. FDA recently issued an initiative and draft guidelines to promote the development of experimental therapeutics in combination to improve the efficacy and safety profile of cancer drug regimens because many of the standard chemotherapeutic agents are highly cytotoxic that elicit severe side effects. Thus, there remains a need to develop new cancer drugs and therapy that are less toxic and effective to treat cancer.

SUMMARY OF THE INVENTION

This invention relates to treatment and diagnosis of inflammatory disorders, e.g., autoimmune diseases, using leukotoxin (LtxA), a bacterial protein, as well as to compositions and methods to treat, reduce and prevent HIV infection using LtxA. Shown below are the polypeptide and nucleotide sequences of LtxA.

```
Aggregatibacter actinomycetemcomitans strain
NJ4500 protein sequence
                                           (SEQ ID NO: 1)
MATTSLLNTKQQAAQFANSVADRAKENIDAAKEQLQKALDKLGKTGKKLT

LYIKNYKKGNGLTALIKAAQKLGIEVYHEGKDGPALTNGILNTGKKLLGL

TERGLTLFAPELDKWIQGNKHLSNSVGSTGNLTKAIDKVQSVLGTLQAFL

NTAFSGMDLDALIKARQNGKNVTDVQLAKASLNLINELIGTISSITNNVD

TFSKQLNKLGEALGQVKHFGSFGDKLKNLPKLGNLGKGLGALSGVLSAIS

AALLLANKDADTATKAAAAAELTNKVLGNIGKAITQYLIAQRAAAGLSTT

GPVAGLIASVVSLAISPLSFLGIAKQFDRARMLEEYSKRFKKFGYNGDSL

LGQFYKNTGIADAAITTINTVLSAIAAGVGAASAGSLVGAPIGLLVSAIT

SLISGILDASKQAVFEHIANQLADKIKAWENKYGKNYFENGYDARHSAFL

EDSLKLFNELREKYKTENILSITQQGWDQRIGELAGITRNGDRIQSGKAY

VDYLKKGEELAKHSDKFTKQILDPIKGNIDLSGIKGSTTLTFLNPLLTAG

KEERKTRQSGKYEFITELKVKGRTDWKVKGVPNSNGVYDFSNLIQHAVTR

DNKVLEARLIANLGAKDDYVFVGSGSTIVNAGDGYDVVDYSKGRTGALTI

DGRNATKAGQYKVERDLSGTQVLQETVSKQETKRGKVTDLLEYRNYKLDY

YYTNKGFKAHDELNSVEEIIGSTLRDKFYGSKFNDVFHGHDGDDLIYGYD

GDDRLYGDNGNDEIHGGQGNDKLYGGAGNDRLFGEYGNNYLDGGEGDDHL

EGGNGSDILRGGSGNDKLFGNQGDDLLDGGEGDDQLAGGEGNDIYVYRKE

YGHHTITEHSGDKDKLSLANINLKDVSFERNGNDLLLKTNNRTAVTFKGW

FSKPNSSAGLDEYQRKLLEYAPEKDRARLKRQFELQRGKVDKSLNNKVEE

IIGKDGERITSQDIDNLFDKSGNKKTISPQELAGLIKNKGKSSSLMSSSR

SSSMLTQKSGLSNDISRIISATSGFGSSGKALSASPLQTNNNFNSYANSL

ATTAA

Aggregatibacter actinomycetemcomitans strain
NJ4500 DNA sequence
                                           (SEQ ID NO: 2)
ATGGCAACTACTTCACTGCTAAATACAAAACAGCAAGCTGCACAGTTTGC

AAATTCAGTTGCAGATAGAGCTAAGGAAAATATTGATGCTGCAAAAGAAC

AATTGCAAAAGGCGTTAGATAAATTAGGGAAGACAGGTAAGAAATTAACT

TTATATATCCCTAAGAATTACAAAAAAGGAAATGGTCTTACTGCGCTTAT

AAAAGCAGCACAGAAGTTAGGGATTGAAGTATATCATGAAGGGAAAGACG

GCCCGGCATTAACTAATGGTATTTTAAATACTGGGAAAAAATTACTTGGT

CTTACCGAACGAGGTTTAACTTTATTTGCTCCGGAATTAGATAAATGGAT

TCAAGGTAATAAACATTTAAGTAATTCTGTGGGTAGTACTGGAAATTTGA

CAAAAGCGATAGATAAGGTTCAGAGTGTTCTTGGTACGTTACAAGCGTTT

TTGAACACCGCATTTTCGGGCATGGATTTAGATGCCTTAATTAAAGCCCG

TCAAAATGGTAAAAATGTAACAGATGTACAGCTAGCAAAAGCCAGTCTTA

ACCTGATTAATGAATTGATTGGTACTATTTCTAGCATTACAAATAATGTA

GATACTTTTTCTAAACAACTTAATAAGTTAGGTGAAGCACTAGGACAAGT

AAAACATTTTGGTAGTTTTGGAGATAAATTAAAGAATTTACCTAAGTTAG

GTAATCTTGGAAAAGGTTTAGGTGCATTATCCGGTGTATTGTCGGCTATA

TCAGCGGCTCTATTACTTGCAAATAAAGATGCTGATACTGCAACGAAAGC

AGCGGCTGCAGCTGAATTGACAAATAAAGTGCTAGGTAACATCGGTAAAG

CGATCACACAATACTTGATTGCTCAACGTGCTGCAGCGGGGcTTTCTACT

ACGGGACCTGTCGCAGGGTTAATTGCCTCTGTGGTCAGCTTGGCAATCAG

CCCTTTGTCTTTCCTAGGTATTGCGAAACAATTTGATCGTGCGAGAATGC

TTGAGGAATACTCGAAACGCTTTAAGAAATTTGGTTATAACGGCGATAGT

TTACTTGGTCAATTCTACAAAAATACAGGGATCGCAGATGCTGCGATTAC

AACGATTAACACTGTATTAAGTGCTATTGCAGCAGGGGTTGGTGCAGCCT

CCGCCGGTTCTTTAGTTGGTGCGCCAATCGGTTTGTTAGTGAGTGCGATT

ACCAGCTTAATTTCAGGAATTCTTGATGCTTCTAAACAAGCCGTTTTTGA
```

-continued

```
ACATATCGCGAATCAGCTCGCCGATAAAATTAAAGCATGGGAGAATAAGT

ACGGTAAGAATTACTTTGAAAATGGCTATGATGCCCGTCATTCCGCCTTC

TTGGAAGATTCACTAAAATTATTTAATGAGTTACGTGAAAAATATAAAAC

CGAAAATATATTATCTATCACTCAACAAGGTTGGGATCAGCGCATTGGTG

AATTAGCAGGTATCACTCGTAATGGAGATCGTATTCAAAGTGGTAAAGCT

TATGTGGATTATTTGAAAAAGGGTGAGGAGCTTGCAAAGCATAGCGATAA

ATTCACTAAACAGATTTTAGATCCAATCAAAGGTAATATTGATCTTTCGG

GTATaAAAGGTTCTACCACTCTAACTTTTTTAAATCCGTTGTTAACCGCA

GGTAAGGAAGAACGGAAAACACGTCAGTCAGGTAAATATGAATTTATTAC

TGAATTAAAAGTAAAAGGACGTACCGATTGGAAGGTAAAAGGTGTTCCTA

ATTCTAATGGTGTATATGATTTTTCTAACTTAATTCAACATGCCGTTACA

CGTGATAATAAAGTTCTAGAAGCAAGATTAATTGCTAATTTGGGTGCTAA

AGATGATTATGTTTTGTCGGATCCGGTTCAACAATAGTTAATGCTGGAG

ACGGTTATGATGTGGTGGACTATAGTAAAGGTCgCACCGGTGCATTAACA

ATCGACGGTCGTAATGCTACTAAAGCCGGACAATATAAGGTTGAAAGAGA

TCTTAGCGGTACTCAAGTCTTGCAGGAAACCGTATCAAAGCAAGAAACTA

AACGAGGGAAGGTTACCGATCTACTTGAATATCGTAACTATAAATTAGAT

TACTATTATACGAATAAGGGCTTTAAAGCTCATGATGAATTAAACTCAGT

AGAGGAAATTATCGGCAGCACACTACGTGATAAATTTTATGGTTCTAAAT

TTAATGATGTTTTCCATGGTCACGATGGCGATGATTTGATTTATGGTTAT

GATGGCGATGATCGTTTGTATGGCGATAATGGGAATGACGAAATTCATGG

CGGCCAAGGTAATGATAAGCTCTATGGTGGTGCCGGTAACGATAGGCTCT

TTGGTGAATATGGCAACAACTATCTTGACGGTGGAGAAGGCGACGACCAC

TTAGAGGGAGGCAATGGTTCCGATATTCTAAGAGGTGGAAGTGGCAATGA

TAAGTTGTTTGGAAACCAAGGAGATGATTTACTTGACGGTGGAGAAGGCG

ATGACCAACTTGCCGGTGGAGAAGGAAATGATATTTATGTTTACCGTAAA

GAATATGGGCACCACACTATTACGGAACATAGCGGTGATAAAGATAAATT

ATCATTAGCAAATATCAATCTCAAAGATGTGTCATTTGAGCGTAACGGCA

ATGATCTACTATTGAAAACAAATAATAGAACAGCAGTAACATTTAAAGGA

TGGTTTAGTAAACCTAATTCATCGGCAGGATTAGATGAGTATCAAAGAAA

ACTTCTTGAATACGCACCTGAAAAGGATCGTGCACGACTTAAGAGACAAT

TTGAGTTACAGCGAGGTAAAGTCGACAAATCACTCAATAATAAAGTTGAA

GAAATTATCGGTAAAGATGGGGAGCGGATTACTTCGCAAGACATTGATAA

TCTTTTTGATAAGAGTGGGAACAAAAAGACAATTTCACCTCAAGAGCTTG

CCGGACTTATTAAGAATAAAGGTAAGTCAAGTAGCCTTATGTCTTCTTCT

CGTTCGTCAAGTATGCTTACACAAAAGTCCGGTTTGTCAAATGATATTAG

TCGTATTATTTCAGCAACCAGTGGTTTTGGTTCATCCGGTAAAGCGTTAT

CCGCTTCGCCATTGCAGACCAATAATAACTTTAACTCTTACGCAAATTCG

TTAGCAACTACTGCGGCC
```

One aspect of this invention features a method for treating lymphoma, comprising administering to a subject in need thereof a composition including a therapeutically effective amount of leukotoxin protein to the subject. The lymphoma may include lymphoma cells expressing activated LFA-1, and the leukotoxin binds to the activated LFA-1 on the lymphoma cells and destroys the lymphoma cells by apoptosis or necrosis, thereby treating the lymphoma. The leukotoxin can be prepared from *Aggregatibacter actinomycetemcomitans*. In one embodiment, the leukotoxin comprises, consists essentially of, or consists of the sequence of SEQ ID NO: 1. Examples of lymphoma may include Hodgkin lymphoma, and non-Hodgkin lymphoma, including anaplastic large-cell lymphoma, angioimmunoblastic lymphoma, blastic NK-cell lymphoma, burkitt's lymphoma, burkitt-like lymphoma (small non-cleaved cell lymphoma), chronic lymphocytic leukemia/small lymphocytic lymphoma, cutaneous T-cell lymphoma, diffuse large B-cell lymphoma, enteropathy-type T-cell lymphoma, follicular lymphoma, hepatosplenic gamma-delta T-cell lymphoma, lymphoblastic lymphoma, mantle cell lymphoma, marginal zone lymphoma, nasal T-cell lymphoma, pediatric lymphoma, peripheral T-cell lymphomas, primary central nervous system lymphoma, transformed lymphomas, treatment-related T-cell lymphomas, and waldenstrom's macroglobulinemia.

In an embodiment, the composition may also include a chemotherapeutic agent. The chemotherapeutic agent is selected from the group consisting of idarubicin, cytarabine, etosposide, daunorubicin, mitoxantrone, melphalan, chlorambucil, fludarabine phosphate, cytarabine, and daunorubicin hydrochloride. In one embodiment, the composition may be administered orally, intravenously, intramuscularly, transdermally, intrarectally, or intravaginally.

A second aspect of the invention features a diagnosing method for determining whether a subject has lymphoma. The method includes the steps of obtaining from the subject a test sample that contains white blood cells; contacting the sample with leukotoxin (e.g., SEQ ID NO: 1); and determining the percentage of the white blood cells that bind to the leukotoxin in the sample. The subject is determined to have the disorder if the percentage is at or above a predetermined value. The leukotoxin can be labeled with a detectable agent, such as FITC. The sample can be a blood sample or a biopsy sample. Preferably, the contacting step is conducted at 0-4° C., such as about 0° C. The predetermined value can be one obtained from a control subject that does not have the disorder.

A third aspect of the invention features a method for determining the effectiveness of a treatment in a patient suffering from lymphoma. The method include steps of obtaining a sample that contains white blood cells from a patient that has received a treatment; contacting the sample with leukotoxin (e.g., SEQ ID NO: 1); and determining the percentage of the white blood cells that bind to the leukotoxin in the sample. The treatment is determined to be effective if the percentage is below a predetermined value. Like that in the above-mentioned diagnosing method, the leukotoxin can be labeled with a detectable agent (e.g., FITC); the sample can be a blood sample or a biopsy sample. Also, the contacting step can be conducted at 0-4° C., such as at about 0° C. Here, the predetermined value can be a control value obtained from the patient prior to the treatment.

A fourth aspect of this invention features a method to lymphoma tumor cells in a subject. The method includes identifying a subject having lymphoma, and reducing the level of cells expressing activated LFA-1 using an anti-LFA-1 agent, wherein the anti-LFA-1 agent is a leukotoxin or a chemotherapeutic agent. The leukotoxin can be prepared from *Aggregatibacter actinomycetemcomitans*. In one embodiment, the leukotoxin comprises, consists essentially of, or consists of the sequence of SEQ ID NO: 1. The chemotherapeutic agent is selected from the group consisting of idarubicin, cytarabine, etosposide, daunorubicin, mitoxantrone, melphalan, chlorambucil, fludarabine phosphate, cytarabine, and daunorubicin hydrochloride.

Another aspect of this invention features a composition, e.g., a pharmaceutical composition, that contains the above-mentioned anti-LFA-1 agent such as an anti-cancer chemotherapeutic agent or leukotoxin, and a pharmaceutically acceptable carrier. The composition can be used for the treatment of lymphoma in a subject or in the manufacture of a medicament for the treatment of lymphoma. The chemotherapeutic agent is selected from the group consisting of idarubicin, cytarabine, etosposide, daunorubicin, mitoxantrone, melphalan, chlorambucil, fludarabine phosphate, cytarabine, and daunorubicin hydrochloride. Examples of the anti-LFA-1 agent include a leukotoxin or an antibody. The leukotoxin can be prepared from *Aggregatibacter actinomycetemcomitans*. In one embodiment, the leukotoxin comprises, consists essentially of, or consists of the sequence of SEQ ID NO: 1.

In the aforementioned methods, the cells can be contacted with the anti-LFA-1 agent ex vivo or in vivo. In the latter approach, the anti-LFA-1 agent can be administered to the subject in a pharmaceutical composition comprising the anti-LFA-1 agent and a pharmaceutically acceptable carrier. The composition can be administered orally, intravenously, intramuscularly, transdermally, intrarectally, or intravaginally.

Other important objects and features of the invention will be apparent from the following description of the invention taken in connection with the accompanying drawings in which:

BRIEF DESCRIPTION OF THE DRAWINGS

FIGS. 5A and 5B are diagrams showing the non-negligent effect of increasing the LFA-1 levels on sensitivity to LtxA.

FIG. 6 is a diagram showing the susceptibility of primary leukemia and lymphoma cells to LtxA.

DETAILED DESCRIPTION OF THE INVENTION

Figure 1A:
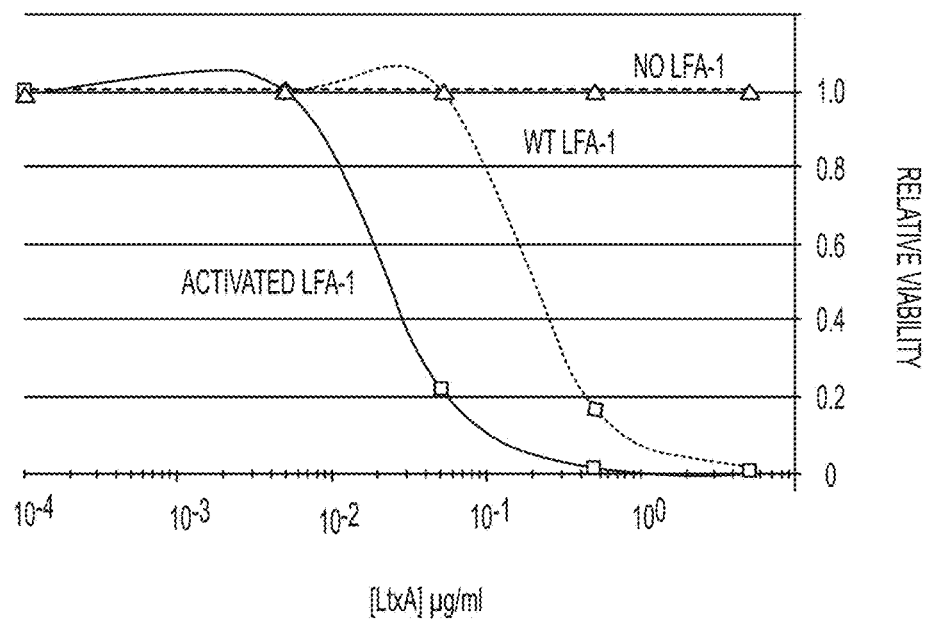
FIGS. 1A and 1B is a set of diagrams showing sensitivity of Jurkat-derived cells (A) and PBMCs (B) to LtxA-mediated cytotoxicity.

The invention provides methods for inducing apoptosis of a cancer cell, particularly lymphoma, comprising contacting the cancer cell with a pharmaceutical compositions comprising leukotoxin n amounts effective to induce apoptosis. Leukotoxin is an effective cell-delivery protein, permeating cancer cells and penetrating to the inside of specific cells.

Not only is leukotoxin capable of penetrating cells, but this penetration is toxic and lethal to cancer cells. The cells treated with leukotoxin are cells that express activated leukocyte function antigen (LFA-1). The cells are generally considered to be hematological cancer cells, cancer related to white blood cells. Examples of hematological cancer cells include without limitation, leukemia, lymphoma, and myeloma. Leukemias include acute myeloid leukemia, chronic myeloid leukemia, acute lymphocytic leukemia and chronic lymphocytic leukemia. Lymphomas include Hodgkin lymphoma, and non-Hodgkin lymphoma, including anaplastic large-cell lymphoma, angioimmunoblastic lymphoma, blastic NK-cell lymphoma, burkitt's lymphoma, burkitt-like lymphoma (small non-cleaved cell lymphoma), chronic lymphocytic leukemia/small lymphocytic lymphoma, cutaneous T-cell lymphoma, diffuse large B-cell lymphoma, enteropathy-type T-cell lymphoma, follicular lymphoma, hepatosplenic gamma-delta T-cell lymphoma, lymphoblastic lymphoma, mantle cell lymphoma, marginal zone lymphoma, nasal T-cell lymphoma, pediatric lymphoma, peripheral T-cell lymphomas, primary central nervous system lymphoma, transformed lymphomas, treatment-related T-cell lymphomas, and waldenstrom's macroglobulinemia. Myelomas include multiple myeloma, extramedullary plasmacytoma, plasmacytomas, and solitary myeloma. Other types of hematological cancer cells are known by one with ordinary skill in the art. In certain embodiments, the hematological cancer is leukemia, lymphoma, myeloma, or any combination thereof. Generally, the cancer also expresses LFA-1.

As used herein, the singular forms "a," "an" and "the" include plural references unless the content clearly dictates otherwise.

The term "about", as used here, refers to +/−10% of a value.

The term "amino acid" refers to natural and/or unnatural or synthetic amino acids, including glycine and both the D and L optical isomers, amino acid analogs (for example norleucine is an analog of leucine) and peptidomimetics.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The term "effective amount," "therapeutically effective amount" or "therapeutic effect" refers to an amount of an antibody, polypeptide, polynucleotide, small organic molecule, or other drug effective to "treat" a disease or disorder in a subject or mammal. In the case of cancer, the therapeutically effective amount of the drug has a therapeutic effect and as such can reduce the number of cancer cells; decrease tumorgenicity, tumorigenic frequency or tumorigenic capacity; reduce the number or frequency of cancer cells; reduce the tumor size; inhibit or stop cancer cell infiltration into peripheral organs including, for example, the spread of cancer into soft tissue and bone; inhibit and stop tumor metastasis; inhibit and stop tumor morbidity and mortality; improve quality of life; or a combination of such effects.

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus those in need of treatment include those already with the disorder; those prone to have the disorder; and those in whom the disorder is to be prevented. In certain embodiments, a subject is successfully "treated" according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity; reduction in the number or frequency of cancer cells; or some combination of effects.

The agent can be administered in vivo or ex vivo, alone or co-administered in conjunction with other drugs or therapy. As used herein, the term "co-administration" or "co-administered" refers to the administration of at least two agent(s) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary.

1. Lymphoma Compositions and Methods

LtxA is a ~115 kDa protein produced by the Gram negative bacterium *Aggregatibacter actinomycetemcomitans* (Kachlany, S. C. 2010. J Dent Res 89:561-570.). LtxA specifically kills leukocytes of humans and old world primates by forming pores in the membrane and causing apoptosis or necrosis (Mangan et al., 1991. Infect Immun 59:3267-72.). LtxA binds specifically to LFA-1 (a $\beta_2$ integrin expressed only on WBCs) and cells that lack LFA-1 are resistant to its toxicity (Kachlany, S. C. et al., 2010. Leukemia Research 34:777-85.). LFA-1 is composed of CD11a and CD18 and involved in immune cell migration and signaling. In the absence of infection, circulating WBCs express a "resting state" LFA-1 on their surface. These WBCs play an essential role in immune surveillance, waiting to be called upon by the immune system. During an infection, WBCs need to migrate to the site of insult to destroy the invading pathogens. Extravasation of WBCs into the infected tissue is mediated by signals, such as cytokines, that are released by host cells at the infection site. Inflammatory cytokines cause LFA-1 to assume an active conformation, which results in binding of activated LFA-1 to intercellular adhesion molecule-1 (ICAM-1) on the surface of endothelial cells. The interaction between LFA-1 and ICAM-1 results in migration of WBCs across the endothelial barrier and into the infected tissue. Similarly, several types of leukemia/lymphoma, including B-cell lymphomas, are dependent on the bone marrow/lymphoid (i.e. spleen and lymph nodes) microenvironment for proliferation and survival. Adhesion molecules, such as LFA-1, play a crucial role in migration of malignant cells and interactions with stromal cells. In addition, this microenvironment not only helps support the proliferation and survival of malignant cells but may also result in de novo drug resistance (Kurtova, A. V. et al. 2009. Blood 113:4604-13).

Activated LFA-1 is an attractive target for treatment of cancer because it is generally only present on WBCs and has been shown to be activated and over-expressed in leukemias and lymphomas (Bechter, O. E. et al., 1999. Leukemia Research 23:483-8; Horst, E. et al. 1991. Leukemia 5:848-53). Studies have also reported that reported that most of the clinical B-cell lymphoma samples they examined were positive for activated LFA-1 (Tanimoto K. et al. 2009. International Journal of Hematology 89:497-507). Others have reported that found that expression of activated LFA-1 correlated with advanced stage and bone marrow infiltration in NHL patients (Terol, M. J. et al. 1999. Journal of Clinical Oncology 17:1869-75).

In addition, targeting LFA-1 with simvastatin was effective at inducing apoptosis of EBV-transformed lymphoblastoid cell lines and treating B-cell lymphoma in mice (Katano, H. et al. 2004. PNAS 101:4960-65). Hence, LtxA represents a new targeted approach for treating lymphomas by selectively binding binds LFA-1 and inducing rapid cell death.

This invention is based, at least in part, on the unexpected discoveries that LtxA efficiently and specifically targets and kills WBCs that express the activated conformation of LFA-1 on their surface while having little or no toxic effect on other cells or organs in the body. As disclosed in the examples below, LtxA is highly effective in treating lymphomas with minimal toxicity because of its target specificity.

Since LtxA is able to identify and kill white blood cells resulting from various types of lymphoma, it is an ideal agent for both the detection and treatment of these conditions. For example, blood from a patient can be analyzed using LtxA-FITC staining. A finding of a large percentage of activated WBCs indicates that the patient should undergo LtxA therapy. The effectiveness of the leukotoxin treatments can be monitored by employing LtxA-FITC reagent that initially diagnosed the disease. As the patient responds positively to treatment, the number of WBCs with upregulated activated surface LFA-1 should be seen to decrease. Further, because of LtxA's highly specific targeting ability, few side effects are expected.

LtxA is able to kill many leukemia and lymphoma cell lines and preclinical studies have shown that it may be an effective targeted therapy for treating hematological malignancies. In non-human primates, it was found that a single LtxA treatment depleted leukocyte counts after only 12 hours and high doses administered to mice were found to be non-toxic.

While many LtxA preparations can be used, highly purified LtxA is preferred. Examples include LtxA polypeptide purified from *Aggregatibacter actinomycetemcomitans* (SEQ ID NO: 1) and other variants having substantially the same biological activity as that having the sequence of SEQ ID NO: 1. It was discovered that *Aggregatibacter actinomycetemcomitans* secreted active LtxA into culture supernatants (Kachlany, S. C., et al. 2000. Infect Immun 68:6094-100) and an efficient method for its purification was described in Kachlany, S. C., et al. 2002. Protein Expr Purif 25:465-71. This method can therefore be used to prepare isolated or purified LtxA polypeptide. In one example, a purification procedure of the toxin involves:

a. inoculating a single colony of *Aggregatibacter actinomycetemcomitans* into a fresh broth and growing cultures;

b. adding the growing cultures to fresh broth, adding glass beads and incubating;

c. centrifuging the incubated culture, forming a pellet and a supernatant;

d. filtering the supernatant through a membrane to provided a filtered supernatant;

e. mixing $(NH_4)_2SO_4$ and the filtered supernatant together to form a mixture;

f. centrifuging the mixture to form a mixture pellet;

g. resuspending the mixture pellet in buffer to form a protein resuspension;

h. passing the protein resuspension through a column; and i. collecting the protein eluting off the column.

See also PCT/US2006/45258 (WO 2007/062150) and US Application 20090075883 (U.S. Ser. No. 12/154,843). The contents of these two documents are incorporated herein by reference in their entireties.

Forms of LtxA include the JP2 form (isolated from the JP2 strain of *Actinobacillus actinomycetemcomitans*) and the NJ4500 form (isolated from the NJ4500 strain of *Actinobacillus actinomycetemcomitans*). The NJ4500 strain of *Actinobacillus actinomycetemcomitans* was deposited with the American Type Culture Collection (ATCC), University Boulevard, Manassas, Va., 20110-2209, USA, as Accession Number PTA-11721 on Mar. 2, 2011.

An "isolated polypeptide" refers to a polypeptide that has been separated from other proteins, lipids, and nucleic acids with which it is naturally associated. The polypeptide can constitutes at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide of the invention can be purified from a natural source, produced by recombinant DNA techniques, or by chemical methods. A functional equivalent of LtxA refers to a polypeptide derivative of the LtxA polypeptide, e.g., a protein having one or more point mutations, insertions, deletions, truncations, a fusion protein, or a combination thereof. It retains substantially the activity of the LtxA polypeptide, i.e., the ability to target and kill WBCs that express the activated conformation of LFA-1 on their surface while having little or no toxic effect on other cells or organs in the body. The isolated polypeptide can contain SEQ ID NO: 1 or a functional fragment of SEQ ID NO: 1. In general, the functional equivalent is at least 75% (e.g., any number between 75% and 100%, inclusive, e.g., 70%, 80%, 85%, 90%, 95%, and 99%) identical to SEQ ID NO: 1.

All of naturally occurring LtxA, genetically engineered LtxA, and chemically synthesized LtxA can be used to practice the invention disclosed herein. LtxA obtained by recombinant DNA technology may have the same amino acid sequence as naturally a occurring LtxA (SEQ ID NO: 1) or a functionally equivalent thereof. The term "LtxA" also covers chemically modified LtxA. Examples of chemically modified LtxA include LtxA subjected to conformational change, addition or deletion of a sugar chain, and LtxA to which a compound such as polyethylene glycol has been bound. Once purified and tested by standard methods known in the art, LtxA can be included in a pharmaceutical composition.

The amino acid composition of the LtxA polypeptide described herein may vary without disrupting the ability of the polypeptide to target and kill WBCs. For example, it can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in SEQ ID NO: 1 is preferably replaced with another amino acid residue from the same side chain family. Alternatively, mutations can be introduced randomly along all or part of SEQ ID NO: 1, such as by saturation mutagenesis, and the resultant mutants can be screened for the ability to improve skin condition to identify mutants that retain the activity as described below in the examples.

A LtxA polypeptide as described in this invention can be obtained as a naturally occurring polypeptide or a recombinant polypeptide. To prepare a recombinant polypeptide, a nucleic acid encoding it (e.g., SEQ ID NO: 2) can be linked to another nucleic acid encoding a fusion partner, e.g., glutathione-s-transferase (GST), 6×-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention.

In an embodiment, a chemotherapeutic pharmaceutical may be administered to the subject in conjuction with the leukotoxin. Some appropriate chemotherapeutic pharmaceuticals include idarubicin, cytarabine, etosposide, daunorubicin, mitoxantrone, and melphalan. Other common chemotherapeutic agents for the treatment of leukemia and lymphoma include Chlorambucil, Fludarabine phosphate, Cytarabine, and Daunorubicin hydrochloride. These drugs share the common property of being highly toxic to humans, affecting many different tissue and organ systems of the body. Bone marrow suppression, severe neurologic effects, infertility, pulmonary, and gastrointestinal effects are some of the adverse effects exhibited by these drugs. Many of the drugs act by inhibiting DNA synthesis, a process that all dividing cells carry out. Most cells of the body are targeted by these non-specific pharmaceuticals. Any suitable pharmaceutical agent may be used in conjunction with LtxA, and the combination of a pharmaceutical agent with leukotoxin is intended to reduce the dose of the pharmaceutical necessary to achieve effective results in patients.

Within the scope of this invention is a composition that contains a suitable carrier and one or more of the active agents described above, e.g., LtxA. The composition can be a pharmaceutical composition that contains a pharmaceutically acceptable carrier.

The term "pharmaceutical composition" refers to the combination of an active agent with a carrier, inert or active, making the composition especially suitable for diagnostic or therapeutic use in vivo or ex vivo. The term "pharmaceutically acceptable carrier" refers to any of the standard pharmaceutical carriers, such as a phosphate buffered saline solution, water, emulsions, and various types of wetting agents. The compositions also can include stabilizers and preservatives. A pharmaceutically acceptable carrier, after administered to or upon a subject, does not cause undesirable physiological effects. The carrier in the pharmaceutical composition must be "acceptable" also in the sense that it is compatible with the active ingredient and, preferably, capable of stabilizing it. One or more solubilizing agents can be utilized as pharmaceutical carriers for delivery of an active agent. Examples of other carriers include colloidal silicon oxide, magnesium stearate, cellulose, and sodium lauryl sulfate.

In an in vivo approach, LtxA is administered to a subject by various methods that may include continuous or intermittent administration, depending on the nature of the cancer. The pharmaceutical compositions of the instant invention may be administered by routes independently selected from the group consisting of oral administration, intravenous administration, intraarterial administration, intramuscular administration, intracolonic administration, intracranial administration, intrathecal administration, intraventricular administration, intraurethral administration, intravaginal administration, subcutaneous administration, intraocular administration, intranasal administration, and any combinations thereof. Accordingly, the pharmaceutically effective compositions may also include pharmaceutically acceptable additives, carriers or excipients. Such pharmaceutical compositions may also include the active ingredients formulated together with one or more non-toxic, pharmaceutically acceptable carriers specially formulated for oral administration in solid or liquid form, for parenteral injection or for rectal administration according to standard methods known in the art.

The term "parenteral" administration refers to modes of administration which include intravenous, intramuscular, intraperitoneal, intracisternal, intrasternal, subcutaneous and intraarticular injection and infusion. Injectable mixtures are known in the art and comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form may be brought about by the inclusion of agents which delay absorption such as aluminum monostearate and gelatin. Injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

In some cases, to prolong the effect of the drug, it is desirable to slow drug absorption from subcutaneous or intramuscular injection. This may be accomplished by using a liquid suspension of crystalline or amorphous material with poor water solubility. The rate of absorption of the drug then depends upon its rate of dissolution which, in turn, may depend upon crystal size and crystalline form. Alternatively, absorption of a parenterally administered drug form may be delayed by dissolving or suspending the drug in an oil vehicle.

To prepare the pharmaceutical compositions of the present invention, an effective amount of the aforementioned agent(s) can be intimately admixed with a pharmaceutically acceptable carrier according to conventional pharmaceutical compounding techniques to produce a dose. A carrier may take a wide variety of forms depending on the form of preparation desired for administration, e.g., oral or parenteral. The agent can be administered in vivo or ex vivo, alone or co-administered in conjunction with other drugs or therapy. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary.

In an in vivo approach, the above-described agent, e.g., LtxA, is administered to a subject. Generally, LtxA is suspended in a pharmaceutically-acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily. In an ex vivo approach, a subject's blood can be withdrawn and treated with the above-mentioned agent to remove cells expressing activated LFA-1 before the blood thus-treated is given back to the subject.

The dose of the pharmaceutical composition of the present invention is determined according to the age, body weight, general health condition, sex, diet, administration time, administration method, clearance rate, and the level of disease for which patients are undergoing treatments at that time, or further in consideration of other factors. While the daily dose of the compound of the present invention varies depending on the condition and body weight of patient, the kind of the compound, administration route and the like, it is parenterally administered at, for example, 0.01 to 100 mg/patient/day by subcutaneous, intravenous, intramuscular, transdermal, transocular, transpulmonary bronchial, or transnasal administration. Variations in the needed dosage are to be expected in view of the variety of compounds available and the different efficiencies of various routes of administration. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery.

Oral dosage forms may include capsules, tablets, emulsions and aqueous suspensions, dispersions, and solutions. In the case of tablets, commonly used carriers include, but are not limited to, lactose and corn starch. Lubricating agents, such as, but not limited to, magnesium stearate, also are typically added. For oral administration in a capsule form, useful diluents include, but are not limited to, lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

In particular examples, an oral dosage range is from about 1.0 to about 100 mg/kg body weight administered orally in single or divided doses, including from about 1.0 to about 50 mg/kg body weight, from about 1.0 to about 25 mg/kg body weight, from about 1.0 to about 10 mg/kg body weight (assuming an average body weight of approximately 70 kg; values adjusted accordingly for persons weighing more or less than average). For oral administration, the compositions are, for example, provided in the form of a tablet containing from about 50 to about 1000 mg of the active ingredient, particularly about 75 mg, about 100 mg, about 200 mg, about 400 mg, about 500 mg, about 600 mg, about 750 mg, or about 1000 mg of the active ingredient for the symptomatic adjustment of the dosage to the subject being treated.

2. Diagnostic and Prognostic Methods

As discussed above, LFA-1, present on WBCs of cancer patients, can act as a marker to detect and monitor the treatment of these afflictions while providing a therapeutic target for pharmaceutical agents. LtxA specifically targets WBCs that express the activated conformation of LFA-1, and therefore can be used in diagnosing diseases meditated by such WBCs.

To that end, this invention also features diagnosis methods. WBCs expressing the activated conformation of LFA-1 can be detected in a subject based on the presence of the binding of LtxA in a test sample from the subject. In other words, the binding of LtxA can be used as markers to indicate the presence or absence of WBCs involved in cancer, including lymphomas. Diagnostic and prognostic assays of the invention include methods for assessing the binding level of LtxA with WBCs.

The binding level in a test sample can be evaluated by obtaining a test sample from a test subject and contacting the test sample with LtxA. The "test sample" includes tissues, cells and biological fluids isolated from a subject, as well as tissues, cells and fluids present within a subject. The level of binding of LtxA to WBCs can be measured in a number of ways, including that described in the examples below. In a preferred embodiment, LtxA or its fragments that mediate binding between LtxA and LFA-1 (i.e., probes) are labeled with a detectable agent. The term "labeled" is intended to encompass direct labeling of the probe by physically linking a detectable substance to the probe, as well as indirect labeling of the probe by reactivity with a detectable substance. For example, LtxA (or its fragment) can be indirectly labeled using a second antibody directed against LtxA, wherein the second antibody is coupled to a detectable substance. Examples of detectable substances or labels include radio isotopes (e.g., $^{125}$I, $^{131}$I, $^{35}$S, $^{3}$H, or $^{32}$P), enzymes (e.g., alkaline phosphatase, horseradish peroxidase, luciferase, or β-glactosidase), fluorescent moieties or proteins (e.g., fluorescein isothiocyanate, rhodamine, phycoerythrin, GFP, or BFP), or luminescent moieties (e.g., Qdot™ nanoparticles by the Quantum Dot Corporation, Palo Alto, Calif.).

LtxA not only binds to, but also kills, WBCs. In the diagnostic or prognostic method, to minimize any potential errors caused by cell death, the binding of LtxA and WBCs can be conducted at low temperatures (e.g., 0-4° C.) and for a short period of time such as 5 to 20 or 30 minutes.

The prognostic assays described herein can be used to determine whether a subject is suitable to be administered with an agent (e.g., a drug) to treat lymphoma. Accordingly, the condition and behavior of a known drug or combination of drugs in the presence of blood samples from different lymphoma patients may be measured and determined. For example, neutralizing antibody in a patient's blood against a potential drug might allow a clinician to exclude the drug from the therapeutic regimen. Excluding an otherwise ineffective drug might greatly reduce unwanted side effects. Indeed several studies have shown a correlation between in vitro chemosensitivity of tumor cells and therapy outcome (Samson, D. J. J. Seideneld, Journal of Clinical Oncology 22:3618-3630). Such correlations could allow the development of assay-directed individualized chemotherapy regimens. Thus the assay of the invention can be used in the following ways:

1. Screening novel drugs for anti-lymphoma/cancer activity.
2. Determine the best drug dosage for a lymphoma/cancer patient.
3. Determine which drug might be most effective for a lymphoma/cancer patient.

Thus, also featured in this invention is a method of monitoring a treatment for cancer (e.g., lymphoma) in a subject. For this purpose, the binding level between LtxA and WBCs can be determined for test samples from a subject before, during, or after undergoing a treatment. A decrease in the binding level after the treatment indicates that the subject can be further treated by the same treatment.

Information obtained from practice of the above assays is useful in prognostication, identifying progression of, and clinical management of diseases and other deleterious conditions affecting an individual's health status. The information more specifically assists the clinician in designing therapy or other treatment regimes to treat cancers, including lymphomas.

The invention now being generally described, it will be more readily understood by reference to the following examples, which are included merely for purposes of illustration of certain aspects and embodiments of the present invention, and are not intended to limit the invention.

Example 1: Purification of LtxA from the NJ4500 Strain of *A. actinomycetemcomitans*

The JP2 strain of *A. actinomycetemcomitans* produces abundant LtxA, but it does not represent a fresh clinical isolate. Here, LtxA was purified from the clinical isolate NJ4500 of *A. actinomycetemcomitans*. This strain also produces and secretes a large amount of LtxA, but the cells adhere to surfaces instead of growing planktonically. This type of adherent growth results in a relatively low number of cells per volume. The cell density of adherent cells was increased by increasing the surface area on which the cells can grow through the addition of spherical glass beads. Soda lime beads provided the greatest amount of LtxA when compared to Pyrex glass beads. The amount of LtxA that was purified from NJ4500 in the presence of soda lime beads was approximately twice that of JP2.

It is important to note that growth of *A. actinomycetemcomitans* in the presence of both types of glass beads was similar suggesting that differences in LtxA quantity was not due variable growth. *A. actinomycetemcomitans* strains JP2 and NJ4500 are known in the art. All bacteria were grown in *A. actinomycetemcomitans* growth medium (AAGM) as known in the art. Plates were incubated at 37° C. in 10% CO2 for 4 days. Broth cultures were incubated for 24 h unless otherwise noted.

LtxA was isolated from JP2 by growing cells in 5 ml AAGM broth for 7-9 h and then diluted into 400 ml fresh AAGM broth. These cultures were then grown for 13-17 h before harvesting supernatant. To obtain supernatant, cultures were centrifuged at 17,000 g for 10 minutes at 4 8 C.

The supernatant was filtered through a 0.22 mm low-protein binding membrane filter. For every 100 ml of filtered supernatant, 32.5 g $(NH_4)_2SO_4$ was added. The mixture was gently rocked at 4 8 C for 1 h. The precipitated protein was collected by centrifugation at 10,000 g for 20 min at 4 8 C. The pellet from 400 ml supernatant was then resuspended in 2 ml LtxA buffer (20 mM Tris-HCl, pH 6.8, 250 mM NaCl, and 0.2 mM $CaCl_2$).

The resuspended pellet was loaded on a column packed with 40 ml of SEPHADEX G-100 (Sigma, St. Louis, Mo.). Protein was eluted in 1 ml fractions with LtxA buffer. Protein content in each fraction was determined with the Bradford reagent. The three fractions with the highest protein content were combined, aliquoted and stored at −80° C. The purity of LtxA was determined on a 4-20% SDS-PAGE gel and the concentration was determined by the BCA assay according to the manufacturer's protocol (Pierce, Rockford, Ill.).

LtxA was purified from the adherent strain NJ4500 by first growing cells in tubes filled with 5 ml AAGM broth for 14 h and then transferring 20 ml of growing cultures into 400 ml AAGM broth in a 500-ml bottle. Prior to adding 400 ml sterile AAGM broth to the 500 ml-bottle, 300 g of glass beads (or no beads, for controls) were autoclaved inside the bottle. The soda lime beads were obtained from Fisher Scientific (cat. 11-312C) and pyrex beads from Corning Incorporated (cat. 7268-5). The inoculated bottle was grown for 36-40 h as described above. During growth, the bottle was inverted several times to allow adherent cells to coat all the beads. After growth, the broth was removed and centrifuged and processed as described above for JP2 LtxA. For these experiments, cells were not removed from the beads.

Although adherent variants such as NJ4500 retain a greater amount of LtxA than the nonadherent variants, a large amount of secreted LtxA from NJ4500 can still be harvested. Because NJ4500 attaches avidly to surfaces, the number of growing cells per volume can be increased by adding 5 mm glass beads to the growth medium. In methods using one of two different types of glass beads, Pyrex and soda lime, the yield of LtxA from cells growing on Pyrex was significantly reduced when compared to the control of no glass beads or soda lime beads.

Example 2: LtxA Specificity Towards WBCs Expressing Activated Surface LFA-1

One hypothesis why some cells are more sensitive to LtxA than others is that LtxA recognizes the activated form of LFA-1 better than LFA-1 in the resting state. To test this, an assay was carried out using Jurkat T-cell line that expresses a high level of constitutively active LFA-1 (J-$\beta_{2.7}$/LFA-1$\Delta$). As controls, isogenic cell lines that either express the wild type form of LFA-1 (J-$\beta_{2.7}$/LFA-1 wt) or lack LFA-1 expression completely (J-$\beta_{2.7}$/mock) were used. It was found that cells with activated LFA-1 were ten times more sensitive to LtxA-mediated toxicity than cells with resting state LFA-1 and LFA-1-deficient cells were not affected by the toxin (FIG. 1A). Thus, LtxA is more toxic towards WBCs expressing activated form of LFA-1, which are the same type of cells that are predominantly present in a lymphoma tumor.

Figure 1B:
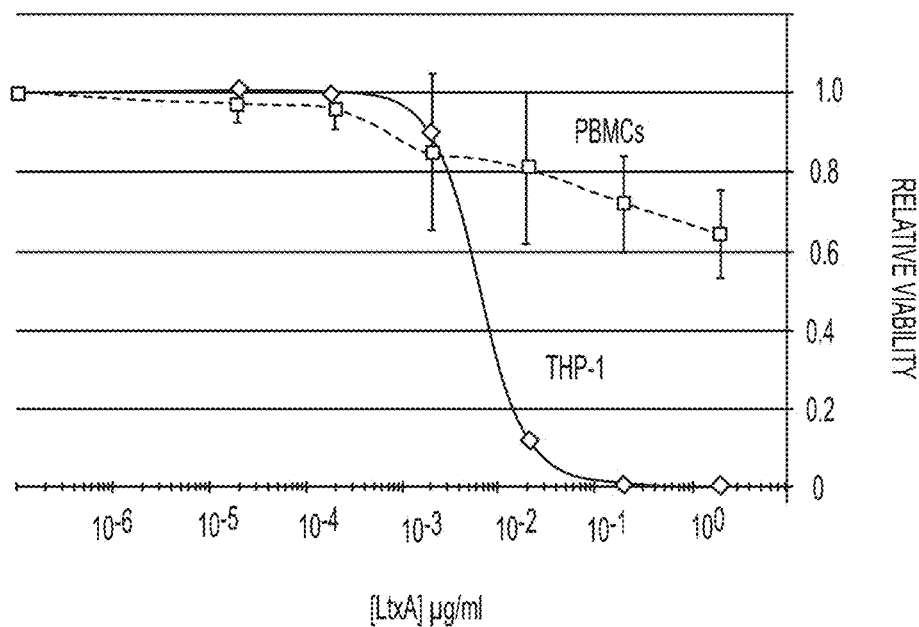
Figures 2A, 2B, 2C:
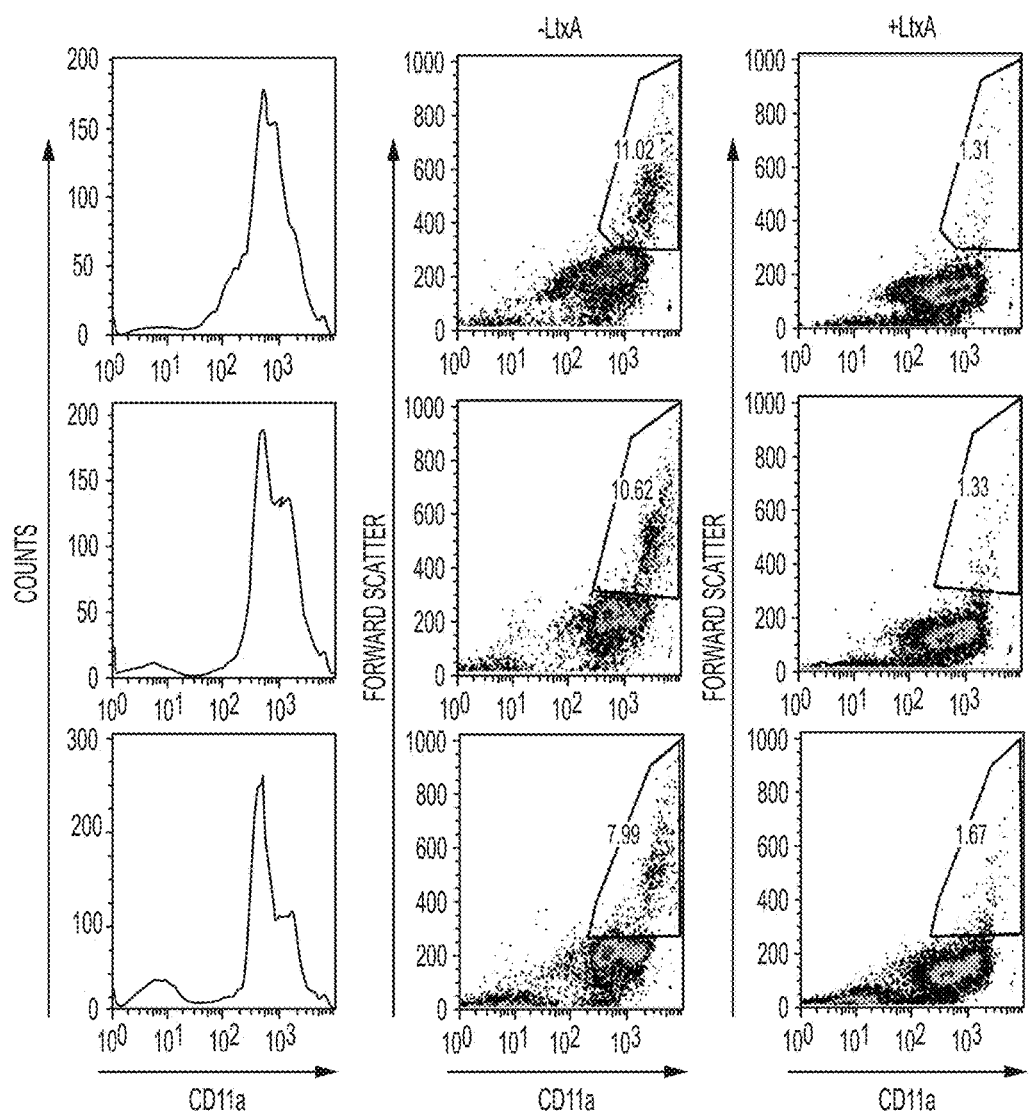
FIGS. 2A, 2B and 2C is a set of diagrams showing flow cytometry results of healthy human PBMCs' staining with anti-LFA-1 antibody and sensitivity to LtxA.

In another experiment, the specificity of LtxA for activated PMBCs was examined. Malignant human monocyte cell line, THP-1, and peripheral blood mononuclear cells (PBMCs) PBMCs from four healthy adults were also treated with LtxA at different concentrations for 24 hours. Cell viability was then determined by measurement of cellular ATP. The results are shown in FIG. 1B. Untreated samples represent a relative viability of 1.0. The curve for PBMCs represents the average of the four human PBMC samples performed in quadruplicate. The vertical bars represent standard deviation. Results shown are representative of biological duplicates. As shown in FIG. 1B, LtxA had little effect on normal, resting human WBCs by examining its effect on normal PBMCs from healthy donors. The majority of cells were found to be resistant to LtxA and a drop in viability was only observed at very high drug concentrations. PBMCs prepared from healthy adults were also stained with anti-LFA-1 (CD11a) antibodies and analyzed by flow cytometry. Shown in FIG. 2 are results of cell size (forward scatter) vs. CD11a expression after 24-hour treatment with a control ("-LtxA") and LtxA ("LtxA"). As shown in the figures, only the activated cells with high levels of LFA-1 were affected by LtxA.

To determine whether LtxA can detect cells that had activated LFA-1 on their surface, purified LtxA was covalently labeled with a fluorescent substituent, fluorescein isothiocyanate (FITC). This allowed the LtxA to be detected and quantified by fluorescence spectroscopy when used in cell binding experiments. Laboratory studies showed that the LtxA-FITC retained full targeting and biological activity indicating that the FITC modification did not adversely affect toxin structure. Test cells were mixed with LtxA-FITC for 30 minutes at 0° C. (on ice) and the resulting conjugates were analyzed by flow cytometry.

Figure 3:
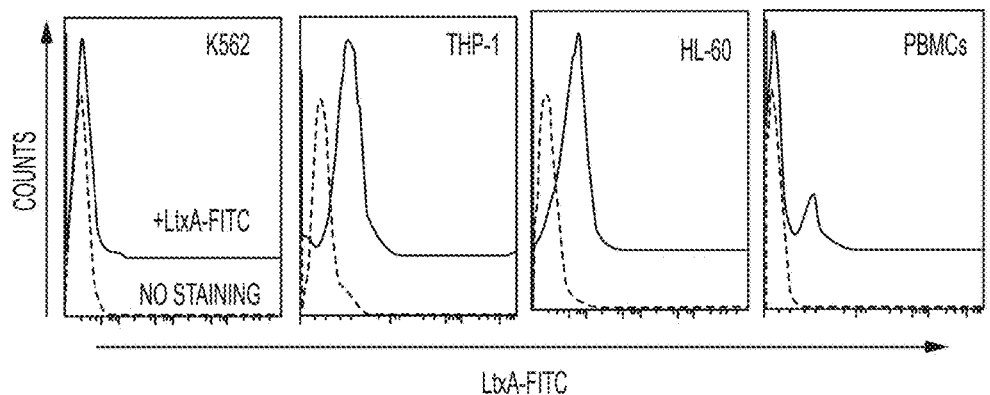
FIG. 3 is a set of diagrams showing flow cytometry results of cells staining with LtxA-FITC.

The test cells included K562 cells (which do not express LFA-1 and are unaffected by LtxA), THP-1 cells, HL-60 cells, and PBMCs (from a healthy donor). As shown in FIG. 3, LtxA-FITC did not kill the test cells due to the low temperatures and brief time period used. Further observations determined that K562 cells (which lack CD11a and CD18) did not bind the leukotoxin-FITC, indicating that LFA-1 is required for cell staining. In contrast, LtxA-FITC strongly attached itself to THP-1 cells and with slightly less intensity to HL-60 cells. Similar experiments were carried out with PBMCs, which possess minimal levels of activated surface LFA-1. As expected, it was found that only a small subset of the PBMCs were stained. These results demonstrate that LtxA binds to specific WBCs and that LtxA targets only cells with activated surface LFA-1.

Figure 4:
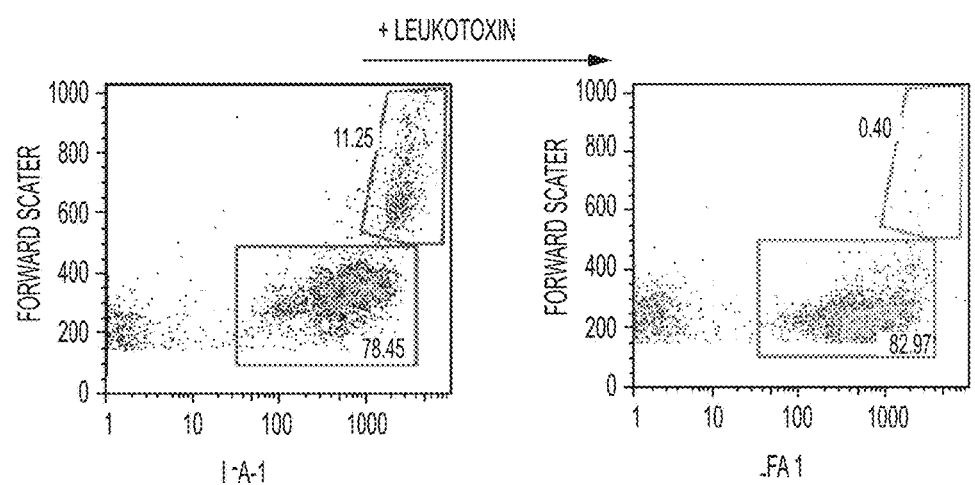
FIG. 4 is a set of flow cytometry histograms showing that LtxA treatment depleted LFA-1$^{hi+}$ cells from PBMCs of healthy donor.

The data presented above using the Jurkat cell lines demonstrates that LtxA prefers the activated form of LFA-1 as a target. Furthermore, based on results showing that only a small fraction of healthy PBMCs are affected by LtxA, it is possible that the killed cells represent the small fraction of activated cells in the population. To test this hypothesis, assays were carried out to determine if LtxA retained this specificity for activated LFA-1 in a sample of PBMCs from healthy individuals. After treatment of PBMCs with LtxA, cells were stained for CD3, CD4, and LFA-1, fixed, and analyzed by flow cytometry. It was found that approximately 11% of the CD3+ T lymphocyte population expressed high levels of LFA-1 while 78% expressed low levels (the remaining did not express LFA-1) prior to treatment with LtxA (FIG. 4). Following LtxA treatment, the high LFA-1-expressing cells were almost completely eliminated (a decrease to 0.4%) while the lymphocytes expressing low-levels of LFA-1 (or not expressing LFA-1) were essentially unaffected. The LFA-1$^{hi+}$ cell population consisted of 96% $CD3^+$ $CD4^+$ T-cells. These results show that LtxA is able to selectively kill activated $CD4^+$ T-lymphocytes in a mixture of PBMCs, suggesting that newly HIV-exposed or infected T-cells would be desired targets for LtxA.

Example 3: LtxA Activity Towards Lymphoma Cell Lines

It was known that LFA-1 plays a crucial role in lymphoma cell proliferation. LtxA may therefore be a valuable therapy for the treatment of lymphoma. In this example, in vitro specificity and activity of LtxA towards various hematological cancer cell lines was demonstrated. Various assays were carried out to determine the concentration of LtxA required to kill 50% of the cells ($IC_{50}$ values) after a 24-hour incubation. To determine $IC_{50}$ values, human cells (~$10^6$ cells/ml) were mixed with purified LtxA at various concentrations. The mixture was incubated at 37° C., 5% $CO_2$ for 24 hours. Cellular viability (ATP production) was then determined using the CellTiter-Glo luminescent cell viability assay (Promega, Madison, Wis.) according to the manufacturer's instructions. Plates were read in a Synergy HT plate reader in the luminescence mode (Bio-Tek, Winooski, Vt.). Cytotoxicity assays were performed at least three different times. The fraction of dead cells (FDC) remaining after a 24-hour treatment with 2.0 µg/ml of the LtxA toxin was also determined. Table 1 shows representative $IC_{50}$ and FDC values obtained from three independent experiments showing the cell lines that are sensitive to LtxA. As shown in Table 1, LtxA is able to cause apoptosis of numerous hematological malignant cell lines including lymphoma (RL and Toledo cells are B-cell lymphoma cell lines, and U937 is a hystiocystic lymphoma cell line).

TABLE 1

| Disease/Cell Line | $IC_{50}$ Value | FDC[1] | CD11a[2] | CD18[2] |
|---|---|---|---|---|
| Acute myeloid leukemia | | | | |
| HL-60 | 200 ng/ml | >99 | 90 | 90 |
| THP-1 | 8 ng/ml | >99 | 96 | 95 |
| GDM-1 | 200 ng/ml | 98 | ND[3] | ND |
| CMK | >10 µg/ml | ND | ND | ND |
| Acute lymphoblastic leukemia | | | | |
| Jurkat | 200 ng/ml | >99 | ND | ND |
| Loucy | 300 ng/ml | 67 | 32 | 89 |
| Molt-4 | 30 ng/ml | 93 | ND | ND |
| Chronic myelogenous leukemia | | | | |
| KU812 | 300 ng/ml | 96 | ND | ND |
| K562 | >10 µg/ml | ND | <1 | <1 |
| MEG-01 | >10 µg/ml | ND | ND | ND |
| Non-Hodgkin's lymphoma | | | | |
| RL | 50 ng/ml | >99 | ND | ND |
| Toledo | 5 ng/ml | 81 | 85 | 86 |
| Histiocytic lymphoma | | | | |
| U937 | 80 ng/ml | 97 | ND | ND |

[1]FDC—Fraction of dead cells after 24-treatment with 2.0 µg/ml LtxA percent dead
[2]Percent positive
[3]ND—Not determined In another experiment, to determine the importance of LFA-1 levels for sensitivity to LtxA, RL cells were treated with IL-4 to increase the surface expression of LFA-1 (FIG. 5A). While this treatment resulted in an almost 10-fold increase in the receptor levels, there was no change in the sensitivity of the cells to LtxA (FIG. 5B). Thus, as shown in FIG. 5B, even low levels of LFA-1 expression on the lymphoma cells are sufficient for LtxA-mediated cytotoxicity.

FIG. 6 shows the cytotoxic effects of LtxA against primary cells from a variety of diseases. As shown in FIG. 6, primary cells from acute myeloid leukemia (AML), acute lymphocytic leukemia (ALL), mantle cell lymphoma (MCL), diffuse large B-cell lymphoma (DLBL), and follicular lymphoma (FLL) patients were all highly sensitive to LtxA as a single agent. It was found that cells that were isolated from relapsed or refractory patients also exhibit high susceptibility to LtxA. These results demonstrate that LtxA has a strong specificity towards malignant lymphocytes (of various malignancies including lymphoma) to cause apoptosis.

Figure 7:
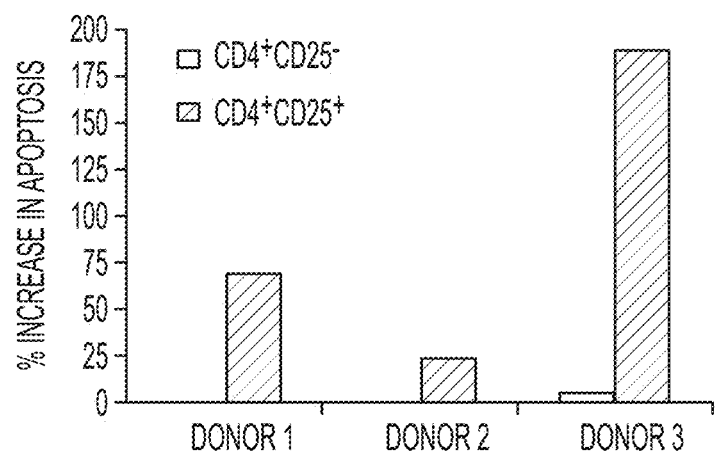
FIG. 7 is a diagram showing the susceptibility of activated T-cells to LtxA.

To further determine specificity of LtxA towards malignant cells lines, Peripheral blood mononuclear cells (PBMCs) from three different human donors were treated with LtxA (40 ng/ml) for 2 hours. Cells were stained with anti-CD4/CD25 antibodies and Annexin V (indicating apoptosis) and analyzed using flow cytometry. All samples were normalized to buffer treatment, and at least 20,000 cells were analyzed per sample. The values of CD4+CD25− cells from donors 1 and 2 were slightly less than 1. It was determined that activated lymphocytes are significantly more sensitive to LtxA than healthy, resting cells. FIG. 7 shows that CD25+ T-cells (activated) are preferentially killed by LtxA compared to non-activated (CD25−) cells. Hence, it was established that LFA-1 is highly expressed and activated on malignant cells, while resting cells (non-activated) have low levels of activated LFA-1.

Figure 8:
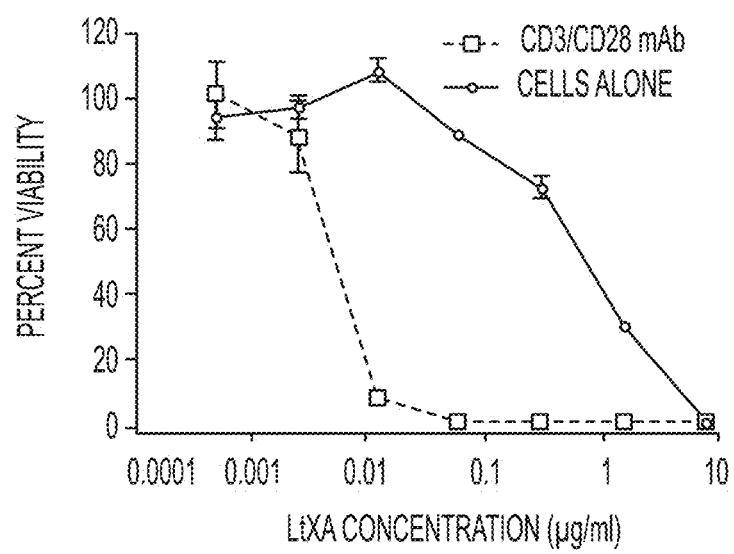
FIG. 8 is a diagram showing the specificity of LtxA targets towards cells expressing activated surface LFA-1.

In addition, CD4 T cells were incubated on wells coated with anti-CD3 and anti-CD28 antibodies (5 µg/ml each) in order to activate lymphocytes, and treated with the designated concentrations of LtxA. FIG. 8 shows that stimulation with anti-CD3/CD28 antibodies to activate lymphocytes increased cell susceptibility to LtxA by >100 fold (ED50 of 5 ng/ml). These results demonstrate that LtxA binds to specific WBCs and that LtxA targets only cells with activated surface LFA-1.

Example 4: LtxA Mediated Cell Delivery

Figure 9:
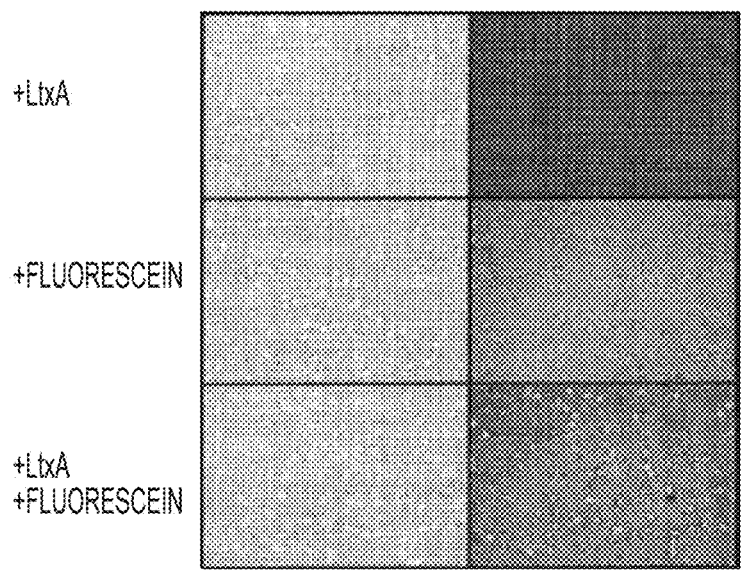
FIG. 9 shows fluorescence microscopy images of leukemia HL-60 cells when exposed to LtxA.

Leukotoxin mediated cell-delivery is demonstrated by introducing fluorescing molecules to specific cells, and measuring cell-delivery by monitoring the fluorescence by fluorescent microscopy. As shown in FIG. 9, the leukotoxin LtxA facilitates delivery of fluorescein into HL-60 leukemia cells. The leukotoxin forms pores or disruptions in the host cell membranes, and these openings in the membrane may allow the passage and entry of small molecules. In FIG. 9, HL-60 cells were treated with fluorescein, a reagent that can be easily tracked by fluorescence microscopy. Fluorescein exhibits a green fluorescence color under the microscope, and is approximately the same molecular weight as many of the cancer drugs currently in use. The cells treated with leukotoxin (LtxA) and fluorescein (FIG. 9, bottom panel) exhibited more intense and abundant fluorescence than the cells treated with fluorescein alone (FIG. 9, center panel), indicating that leukotoxin is able to increase the number of fluorescein molecules that enter the cells.

Not only is leukotoxin capable of penetrating cells, but this penetration is toxic and lethal to HL-60 cells. HL-60 cells were modified to express luciferase genes, and with this HL-60luc system, it was shown that at certain concentrations, leukotoxin is quite toxic to the HL-60luc cells. By monitoring the luminescence of the cells, nearly 80% of the cells were killed by concentrations of leukotoxin as low as 200 ng/ml. See also US Application 20140073586 (U.S. Ser.

No. 14/024,110), the contents of which is incorporated herein by reference in its entirety.

Data reflecting the sensitivity of HL-60luc cells to leukotoxin is shown in FIG. 2. The activity of purified leukotoxin against HL-60luc cells in vitro is quantified. The leukotoxin used in this experiment was LtxA isolated from the NJ4500 strain of *Actinobacillus actinomycetemcomitans*. The LtxA was mixed with HL-60luc cells at various concentrations as indicated, and incubated for two hours, and then imaged with the IVIS 50 instrument. Relative viability was calculated by quantifying the number of photons produced in each well. Significant cell death was observed after two hours for concentrations of 2.0 μg/ml, 0.2 μg/ml, and 0.02 μg/ml.

Figure 10A:
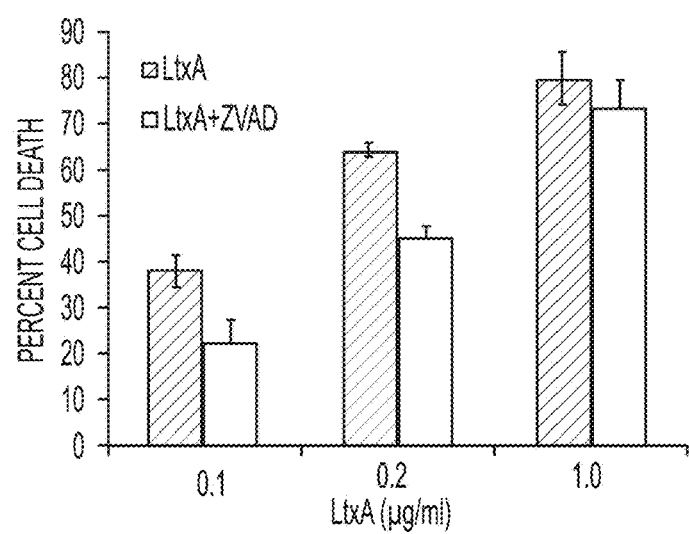
FIG. 10A is a diagram showing the effect of a general caspase inhibitor on LtxA-mediated cell death in RL cells (B-cell lymphoma cell line).
Figure 10B:
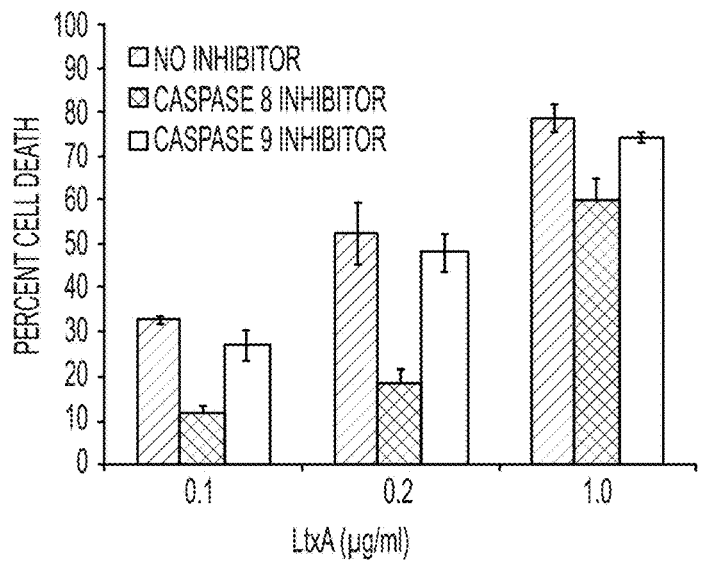
FIG. 10B is a diagram showing the effects of caspase 8 and 9 inhibitors on LtxA-mediated cell death in RL cells.

Experiments were also carried out to study the mechanism of LtxA-mediated cell death of B-cell lymphoma cells. To understand how these cells are depleted by LtxA, effect of inhibitors of apoptosis (caspase inhibitors) were examined. It was found that a general caspase inhibitor like z-VAD-FMK (carbobenzoxy-valyl-alanyl-aspartyl-[O-methyl]-fluoromethylketone) caused a reproducible decrease in cell death proving that caspases are required for LtxA-mediated apoptosis of malignant B-cells (FIG. 10A). However, complete inhibition of cell death was never observed, indicating that other mechanisms are also likely activated by LtxA. It was further determined that caspase 8 (initiator of the extrinsic apoptotic pathway) was most important for LtxA-mediated cell death while caspase 9 (initiator of the intrinsic apoptotic pathway) was not required (FIG. 10B). The results indicate that LtxA may turn LFA-1 into a death receptor since caspase 8 is usually associated with a death receptor.

Example 5: In Vivo Activity of LtxA on Malignant Cells

LtxA Efficacy in a B-Cell Lymphoma Mouse Model.

Figure 11:
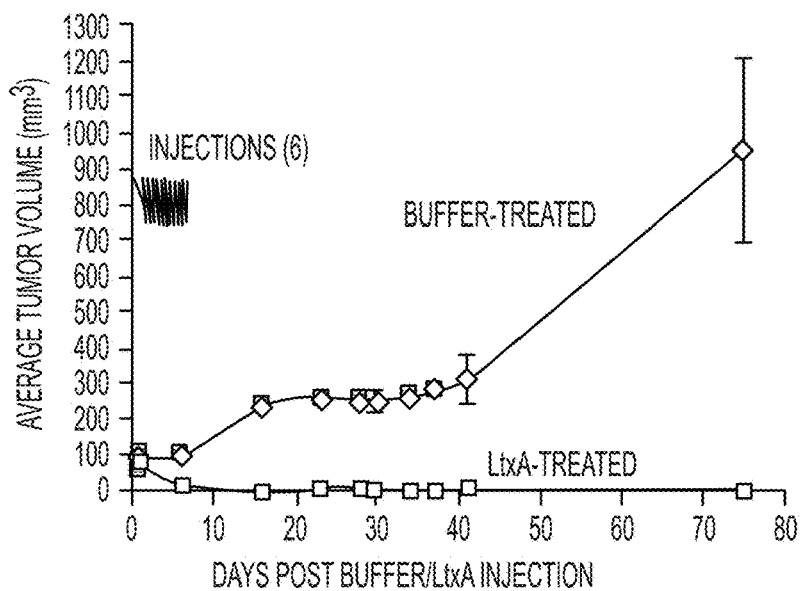
FIG. 11 is a diagram showing in vivo effects of LtxA in a human xenograft B-cell lymphoma mouse model.

To determine if the leukotoxin LtxA has activity in vivo and the ability to treat solid lymphoma tumors, experiments were conducted using a mouse model. RL B-cell lymphoma cells (5 million cells) were injected subcutaneously into NOD-SCID mice and when the resulting tumor volume reached ~100 mm$^3$ (after about 2 weeks to represent later stage of disease), LtxA or buffer vehicle was injected i.p. daily for six consecutive days. FIG. 11 shows the in vivo effects of LtxA in a human xenograft B-cell lymphoma mouse model (n=7). As shown in FIG. 11, the tumors in the buffer-treated mice continued to grow while those in the LtxA-treated mice regressed (FIG. 11). At least, four out of seven of the LtxA-treated mice had complete regression and displayed no visible tumors while the remaining two had tumors that were smaller than 5 mm$^3$. In addition, no observable adverse reactions (such as weight loss, loss of fur, change in behavior, or the like) were observed at any point during the experiment in the LtxA-injected animals. These results indicate that LtxA has very significant anti-lymphoma effects in vivo even when the treatment is commenced after the tumors have been established.

Activity and Safety of LtxA in Dogs.

Figure 12:
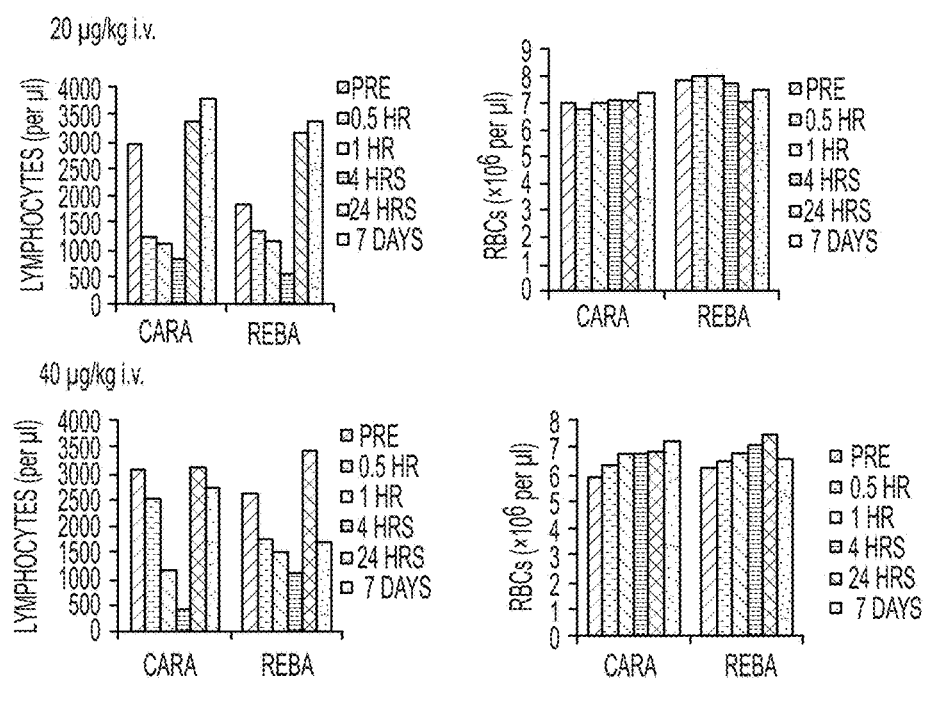
FIG. 12 is a diagram showing in vivo effects of LtxA on lymphocytes and RBCs in two dogs after IV administration.

The physiology and immune system of dogs closely resemble that of humans, and these animals are used extensively for studying new therapeutic agents. In addition, B-cell lymphomas is the most common form of cancer in dogs and in many ways resemble human B-cell lymphomas, making the disease an excellent natural model to study human B-cell cancer. LtxA was administered intravenously (20 μg/kg then 4 μg/kg) into two dogs and a complete blood count analysis was performed (FIG. 12). The drug targeted only a subset of WBCs, and lymphocytes were highly sensitive even at the lowest dose. This targeting was due to the presence of LFA-1 on canine WBCs (data not shown). Red blood cells (RBCs) were not affected and the drug was very well tolerated for the duration of the study. Thus, LtxA may also be for treatment of canine B-cell lymphoma.

Activity of LtxA in Monkeys.

Figure 13:
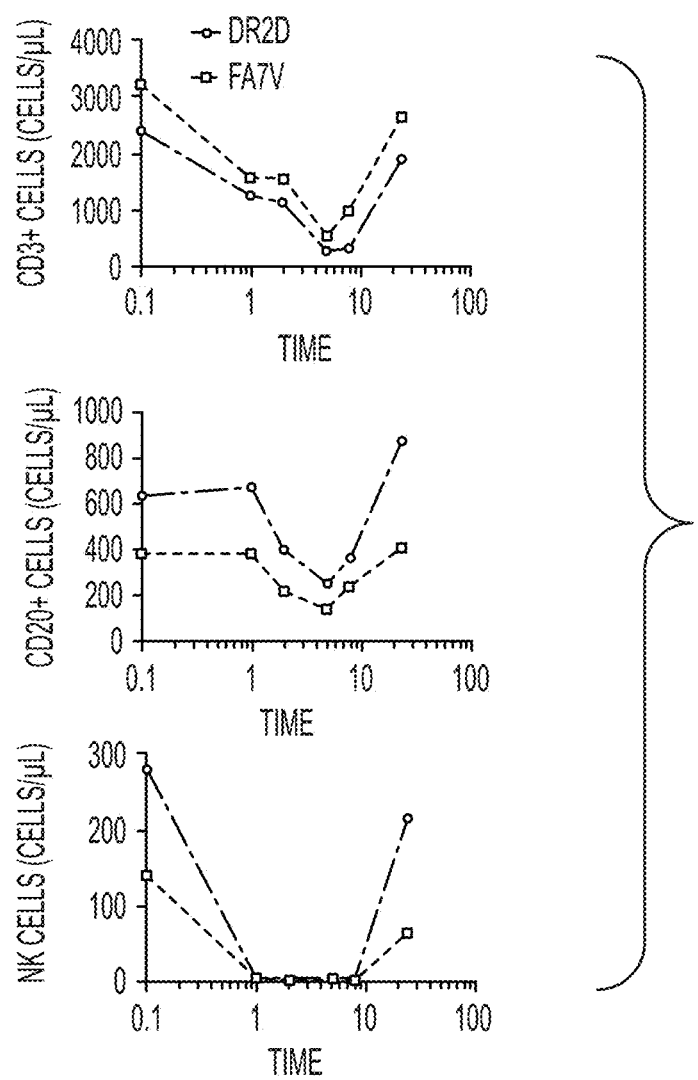
FIG. 13 is a diagram showing in vivo effects of LtxA on lymphocytes in two rhesus monkeys (The first time point represents pre-injection of LtxA, time is in hours (log scale)).

To determine the subpopulations that are affected by LtxA in vivo, immunophenotypic analysis of WBCs in rhesus monkeys was also performed. LtxA (22 μg/kg) was infused i.v. into two monkeys over a twenty-minute period and then blood was drawn from animals at different time points. WBCs were analyzed by flow cytometry. T-cells (CD3$^+$), B-cells (CD20$^+$), and natural killer (NK) cells were depleted by LtxA (FIG. 13).

In sum, the above study demonstrates the in vivo specificity and activity of LtxA towards lymphoma malignant cells.

All publications, including but not limited to patents and patent applications, cited in this specification are herein incorporated by reference as if each individual publication were specifically and individually indicated to be incorporated by reference herein as though fully set forth.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

The invention claimed is:

1. A method of treating lymphoma in a subject in need thereof comprising administering a composition consisting essentially of a therapeutically effective amount of a leukotoxin protein to the subject, wherein said lymphoma comprises lymphoma cells expressing activated leukocyte function antigen (LFA-1), and wherein said leukotoxin binds to said activated LFA-1 on said lymphoma cells and destroys said lymphoma cells by apoptosis or necrosis, thereby treating said lymphoma, and wherein the leukotoxin protein comprises the sequence of SEQ ID NO: 1.

2. The method of claim 1, wherein the composition is administered parenterally or orally.

3. A method of treating lymphoma in a subject in need thereof comprising administering a composition consisting of a therapeutically effective amount of a leukotoxin protein to the subject, wherein said lymphoma comprises lymphoma cells expressing activated leukocyte function antigen (LFA-1), and wherein said leukotoxin binds to said activated LFA-1 on said lymphoma cells and destroys said lymphoma cells by apoptosis or necrosis, thereby treating said lymphoma, and wherein the leukotoxin protein comprises the sequence of SEQ ID NO: 1.

4. A method of treating lymphoma in a subject in need thereof consisting essentially of administering a composition consisting essentially of a therapeutically effective amount of a leukotoxin protein to the subject, wherein said lymphoma comprises lymphoma cells expressing activated leukocyte function antigen (LFA-1), and wherein said leukotoxin binds to said activated LFA-1 on said lymphoma cells and destroys said lymphoma cells by apoptosis or necrosis, thereby treating said lymphoma, and wherein the leukotoxin protein comprises the sequence of SEQ ID NO: 1.

\* \* \* \* \*